(12) United States Patent
Hilton et al.

(10) Patent No.: US 6,414,128 B1
(45) Date of Patent: Jul. 2, 2002

(54) HAEMOPOIETIN RECEPTOR AND GENETIC SEQUENCES ENCODING SAME

(75) Inventors: Douglas James Hilton, Warrandyte; Tracy Willson, North Balwyn; Timothy Gainsford, North Carlton; Warren S Alexander, Moonee Ponds; Donald Metcalf; Ashley Ng, both of Balwyn; Nicos A Nicola, Mont Albert, all of (AU)

(73) Assignee: Amrad Operations Pty. Ltd., Victoria (AU)

( * ) Notice: Subject to any disclaimer, the term of this patent is extended or adjusted under 35 U.S.C. 154(b) by 0 days.

(21) Appl. No.: 09/043,816

(22) PCT Filed: Sep. 26, 1996

(86) PCT No.: PCT/AU96/00607

§ 371 (c)(1), (2), (4) Date: Sep. 17, 1998

(87) PCT Pub. No.: WO97/12037

PCT Pub. Date: Apr. 3, 1997

(30) Foreign Application Priority Data

Sep. 26, 1995 (AU) ............................................. PN5641

(51) Int. Cl.⁷ ................................................. C12N 15/12
(52) U.S. Cl. .................. 536/23.5; 435/69.1; 435/252.3; 435/320.1
(58) Field of Search ........................ 435/7.7, 7.2, 69.1, 435/252.3, 320.1, 372.1; 536/23.5

(56) References Cited

U.S. PATENT DOCUMENTS 5,763,211 A * 6/1998 Snodgrass et al. ......... 435/69.1

* cited by examiner

*Primary Examiner*—John Ulm
(74) *Attorney, Agent, or Firm*—Scully, Scott, Murphy & Presser

(57) ABSTRACT

The present invention is directed to a novel haemopoietin receptor or a derivative thereof and to genetic sequences encoding same. The receptor molecule and its derivatives and the genetic sequences encoding same of the present invention are useful in the development of a wide range of agonists, antagonists, therapeutics and diagnostic reagents based on ligand interaction with its receptor. The present invention particularly relates to a receptor for leptin.

6 Claims, 20 Drawing Sheets

```
-255                                                               cgaattcgcggggcgc
-240  gtcgaccgcggnncccagctcggggagacatggggggcgttaaagctctcgtgnattatcc
-180  ttcagtgggggstattggactgactttcttatgctgggatgtgccttagaggattatgga
-120  tttggcagttcaccctgaccatcttgaaaataagttatctctgatctctgtctgtatgtt
 -60  actttctccccctcaccaacggagaacaaatgtgggcaaagtgtacttctctgaagtaag
   1  ATGATTTGTCAAAAATTCTGTGTGGTTTTGTTACATTGGGAATTTATTTATGTGATAACT
   1   M  I  C  Q  K  F  C  V  V  L  L  H  W  E  F  I  Y  V  I  T
  61  GCGTTTAACTTGTCATATCCAATTACTCCTTGGAGATTAAGTTGTCTTGCATGCCACCA
  21   A  F  N  L  S  Y  P  I  T  P  W  R  F  K  L  S  C  M  P  P
 121  AATTCAACCTATGACTACTTCCTTTTGCCTGGACTCTCAAAGAATACTTCAAATTCG
  41   N  S  T  Y  D  Y  F  L  L  P  A  G  L  S  K  N  T  S  N  S
```

Figure 2A

```
181  AATGGACATTATGAGACAGCTGTTGAACCTAAGTTTAATTCAAGTGGTACTCACTTTCT
 61   N  G  H  Y  E  T  A  V  E  P  K  F  N  S  S  G  T  H  F  S

241  AACTTATCCAAAACAACTTTCCACTGTTGCTTTCGGAGTGAGCAAGATAGAAACTGCTCC
 81   N  L  S  K  T  T  F  H  C  C  F  R  S  E  Q  D  R  N  C  S

301  TTATGTGCAGACAACATTGAAGGACATTTGTTTCAACAGTAAATTCTTTTAGTTTTT
101   L  C  A  D  N  I  E  G  R  T  F  V  S  T  V  N  S  L  V  F

361  CAACAAATAGATgCAAAACTGGAACATACAGTGCTGGCTAAAAGGAGACTTAAAATTATTC
121   Q  Q  I  D  A  N  W  N  I  Q  C  W  L  K  G  D  L  K  L  F

421  ATCTGTTATGTGGAGTCATTATTTAAGAATCTATTCAGGAATTATAACTATAAGGTCCAT
141   I  C  Y  V  E  S  L  F  K  N  L  F  R  N  Y  N  Y  K  V  H
```

Figure 2B

```
481  CTTTTATATGTTCTGCCTGAAGTGTTAGAAGATTCACCCTCTGGTTCCCCAAAAAGGCAGT
161   L   L   Y   V   L   P   E   V   L   E   D   S   P   L   V   P   Q   K   G   S

541  TTTCAGATGGTTCACTGCAATTGCAGTGTTCATGAATGTTGTCAATGTCTTGTGCCTGTG
181   F   Q   M   V   H   C   N   C   S   V   H   E   C   E   C   L   V   P   V

601  CCAACAGCCAAACTCAACGACACTCTCCTTATGTGTTtGAAAATCACATCTGGTGGAGTA
201   P   T   A   K   L   N   D   T   L   L   M   C   L   K   I   T   S   G   G   V

661  ATTTTCCrGTCACCTCTAATGTCAGTTCAGCCCATAAATATGGTGAAGCCTGATCCACCA
221   I   F   X   V   T   S   N   V   S   S   A   H   K   Y   G   E   A   D   P   P

721  TTAGGTTTGCATATGGAAATCACAGATGATGGTAATTTAAAGATTTCTTGGTCCAGCCCA
241   L   G   L   H   M   E   I   T   D   D   G   N   L   K   I   S   W   S   S   P
```

Figure 2C

```
781  CCATTGGTACCATTTCCACTTCAATATCAAGTGAAATATTCAGAGAATTCTACAACAGTT
261   P  L  V  P  F  P  L  Q  Y  Q  V  K  Y  S  E  N  S  T  T  V

841  ATCAGAGAAGCTGACAAGATTGTCTCAGCTACATCCCTGCTAGTAGACAGTATACTTCCT
281   I  R  E  A  D  K  I  V  S  A  T  S  L  L  V  D  S  I  L  P

901  GGGTCTTCGTATGAGGTTCAGGTTGAGGGGCAAGAGACTGGAGATGGCCCAGGAATCTGGAGT
301   G  S  S  Y  E  V  Q  V  R  G  K  R  L  D  G  P  G  I  W  S

961  GACTGGAGTACTCCCTCGTGTCTTTTACCACACAAGATGTCATATACTTTCCACCTAAAATT
321   D  W  S  T  P  R  V  F  T  T  Q  D  V  I  Y  F  P  P  K  I

1021 CTGACACAAGTGTTGGGTCTAATGTTTTCTTTTCACTGCATCTATAAGAAGGAAAACAAGATT
341   L  T  S  V  G  S  N  V  S  F  H  C  I  Y  K  K  E  N  K  I
```

Figure 2D

```
1081  GTTCCCTCAAAAGAGATTGTTTGGTGGATGAATTTAGCTGAGAAAATTCCTCAAAGCCAG
 361    V  P  S  K  E  I  V  W  W  M  N  L  A  E  K  I  P  Q  S  Q

1141  TATGATGTTGTGAGTGATCATGTTAGCAAAGTTACTTTTTTCAATCTGAATGAAACCAAA
 381    Y  D  V  V  S  D  H  V  S  K  V  T  F  F  N  L  N  E  T  K

1201  CCTCGAGGAAAGTTTTACCTATGATGCAGTGTACTGCTGCAATGAACATGAATGCCATCAT
 401    P  R  G  K  F  T  Y  D  A  V  Y  C  C  N  E  H  E  C  H  H

1261  CGCTATGCTGAATTATATGTGATTGATGTCAATATCTCATGTGAAACTGATGGG
 421    R  Y  A  E  L  Y  V  I  D  V  N  I  N  I  S  C  E  T  D  G

1321  TACTTAACTAAAAATGACTTGCAGATGGTCAACCAGTACAATCCAGTCACTTGCGGAAAGC
 441    Y  L  T  K  M  T  C  R  W  S  T  S  T  I  Q  S  L  A  E  S
```

Figure 2E

```
1381  ACTTTGCAATTGAGGTATCATAGGAGCAGCCTTTACTGTTCTGATATTCCATCTATTCAT
 461    T  L  Q  L  R  Y  H  R  S  S  L  Y  C  S  D  I  P  S  I  H

1441  CCCATATCTGAGCCCAAAGATTGCTATTTGCAGAGTGATGGTTTTTATGAATGCATTTTC
 481    P  I  S  E  P  K  D  C  Y  L  Q  S  D  G  F  Y  E  C  I  F

1501  CAGCCAATCTTCCTATTATCTGGCTACACAATGTGGATTAGGATCAATCACTCTCTAGGT
 501    Q  P  I  F  L  L  S  G  Y  T  M  W  I  R  I  N  H  S  L  G

1561  TCACTTGACTCTCCACCAACATGTGTCCTTCCTGATTCTGTGGTGAAGCCACTGCCTCCA
 521    S  L  D  S  P  P  T  C  V  L  P  D  S  V  K  P  L  P  P

1621  TCCAGTGTGAAAGCAGAAATTACTATAAACATTGGATTATTGAAAATATCTTGGGAAAAG
 541    S  S  V  K  A  E  I  T  I  N  I  G  L  L  K  I  S  W  E  K
```

Figure 2F

```
1681  cCAGTCTTTCCAGAGAATAACCTTCAATTCCAGATTCGcTATGGTTTAAGTGGAAAAGAA
561      P  V  F  P  E  N  N  L  Q  F  Q  I  R  Y  G  L  S  G  K  E

1741  GTACAATGGAAGATGTATGAGGTTTATGATCCAAaACCAAAATCTGTCAGTCTCCCAGTT
581      V  Q  W  K  M  Y  E  V  Y  D  P  K  P  K  S  V  S  L  P  V

1801  CCAGACTTGTGTGCAGTCTATGCTGTTCAGGTGCGCTTTAAGAGGCTAGATGGACTGGGA
601      P  D  L  C  A  V  Y  A  V  Q  V  R  F  K  R  L  D  G  L  G

1861  TATTGGAGTAATTGGAGCAATCCAGCCTACACAGTTGTCATGGATATAAAAGTTCCTATG
621      Y  W  S  N  W  S  N  P  A  Y  T  V  V  M  D  I  K  V  P  M

1921  AGAGGACCTGAATTTTGGAGAATAATTAATGGAGATACTATGAAAAAGGAGAAAATGTC
641      R  G  P  E  F  W  R  I  I  N  G  D  T  M  K  K  E  K  N  V
```

Figure 2G

```
1981  ACTTTACTTTGGAAGCCCCTGATGAAAAATGACTCATTGTGCAGTGTTCAGAGATATGTG
 661   T  L  L  W  K  P  L  M  K  N  D  S  L  C  S  V  Q  R  Y  V

2041  ATAAACCATCATACTTCCTsCAATGGAACATGGTCAGAAGATGTGGGAAATCACACGAAA
 681   I  N  H  H  T  S  X  N  G  T  W  S  E  D  V  G  N  H  T  K

2101  TTCACTTTCCTGTGGACAGAGCAAGCACATACTGTTACGGTTCTGGCCATCAATTCAATT
 701   F  T  F  L  W  T  E  Q  A  H  T  V  T  V  L  A  I  N  S  I

2161  GGTGCTTCTGTTgCaAATtTTAACCTTTTCATGGCCtATGAGCAAAGTAAATATC
 721   G  A  S  V  A  N  F  N  L  T  F  S  W  P  M  S  K  V  N  I

2221  GTGCAGTCACTCAGTGCTTATCCTTTAAACAGCAGTTGTGTGATTGTTTCCTGGATACTA
 741   V  Q  S  L  S  A  Y  P  L  N  S  S  C  V  I  V  S  W  I  L
```

Figure 2H

```
2281  TCACCCAGTGATTACAAGCTAAATGTATTTTATTATTGAGTGGAAAAATCTTAATGAAGAT
 761    S   P   S   D   Y   K   L   M   Y   F   I   I   E   W   K   N   L   N   E   D

2341  GGTGAAATAAAATGGCTTAGAATCTCTTCATCTGTGTTAAGAAGTATTATATCCATGATCAT
 781    G   E   I   K   W   L   R   I   S   S   V   K   K   Y   Y   I   H   D   H

2401  TTTATCCCCATTGAGAAGTACCAGTTCAGTCTTTACCCAAtATTTATGGAAGGAGTGGGA
 801    F   I   P   I   E   K   Y   Q   F   S   L   Y   P   I   F   M   E   G   V   G

2461  AAACCAAAGATAATTAATAGTTTCACTCAAGATGATATTGAAAAACACCAGAGTGATGCA
 821    K   P   K   I   I   N   S   F   T   Q   D   D   I   E   K   H   Q   S   D   A

2521  GGTTTATATGTAATTGTGCCAGTAATTATTCCCTCTTCCATCTTATTGCTTGGAACATTA
 841    G   L   Y   V   I   V   P   V   I   I   S   S   I   L   L   L   G   T   L
```

Figure 2I

```
2581  TTAATATCACCAAAGAATGAAAAAGCTATTTTGGAAGATGTTCCGAACCCCAAGAAT
 861   L  I  S  H  Q  R  M  K  K  L  F  W  E  D  V  P  N  P  K  N

2641  TGTTCCTGGCCACAAGGACTTAATTTTCAGAAGAGAACGGACATTCTTtgaagtctaatc
 881   C  S  W  A  Q  G  L  N  F  Q  K  R  T  D  I  L  *

2701  atgatcactacagatgaacccaatgtgccaacttcccaacagtctatagagtattagaag
3761  attttacattttgaagaagggagcaaatctaaaaaaattcagttgaacttctgagag
2821  ttaacatatggtggattatgttgatttagaacttaaaatagatgtcatttaaacccaagt
2881  tttacatctaaactcaggtcaaacctcagttaaaagttttagtagatttcaaatt
2941  ttcatcataagtactaaagaaccgaaaacagtataagttacagtagtttttgtaattc
3001  ttttaataccgacaacgacacagtaatgtatagataatttacagtagtttatcatcatctg
3061  ttaggacattaatccacttgagattttgacgttgtagactgtgtttatcgaaattttatgt
3121  tactaatattcatacctagtcactttttataaatcaaacataaaaatacaggtttgaaaa
```

Figure 2J

```
3181  ggtaaaatctaaggaaatatctgtgcagtcggatttttagtcggataagcccacaagaaa
3241  acttatagaggaccgtaaaaacatagattgaaacaagttagaccctttaaagtcaaaagtt
3301  ataggaacttttaccgaattcactattgaaggcaaagtcaattcctccttcgggcttcaac
3361  acaaacacgacgggtgtcctgtcaccctcaatgtcaagtatagtcctactgggatgtatg
3421  ggtccagtctaactgccctggtcttccctgtagctgaagattacaggtgcgaagaaaca
3481  aattaatactggatttagattaaaatgaaggtgacttggtaggttctggagaccgtccgtc
3541  cctttacccgtcactasgttttttccctctgagaaacctcgaaaatacttatcaagtacc
3601  actcctgtcttgaaaagatgaaagtctgacgaacgatcaaatacttaag
```

Figure 2K

Cross-species conservation of the NR-2 gene

Expression of the Leptin Receptor (NR2) in murine tissues

SEQUENCE LISTING

<160> NUMBER OF SEQ ID NOS: 44

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence:Synthetic

<400> SEQUENCE: 1
rctccartcr ctcca                                                    15

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence:Synthetic

<400> SEQUENCE: 2
taatacgact cactataggg aga                                           23

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:Synthetic

<400> SEQUENCE: 3
attaccctca ctaaaggga                                                19

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:Synthetic

<400> SEQUENCE: 4
actagcaggg atgtagctga g                                             21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:Synthetic

<400> SEQUENCE: 5
ctcagctaca tccctgctag t                                             21

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence:Synthetic

<400> SEQUENCE: 6
ctgctcctat gatacct                                                  17

<210> SEQ ID NO 7
<211> LENGTH: 22

```
<212> TYPE: DNA
<213> ORGANISM: Artificial Sequence
<220> FEATURE:
<223> OTHER INFORMATION: Description of Artificial Sequence:Synthetic

<400> SEQUENCE: 7
cctcttccat cttattgctt gg                                              22

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 8
atcggtcgtg acatacaagg                                                 20

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence:Synthetic

<400> SEQUENCE: 9
agctaagctt tctagatatc caattactcc ttggaga                              37

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence:Synthetic

<400> SEQUENCE: 10
agcttctaga tcaatcactc tggtgttttt caat                                 34

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence:Synthetic

<400> SEQUENCE: 11
acgttctaga tcaaactttt atatccatga caac                                 34

<210> SEQ ID NO 12
<211> LENGTH: 3909
<212> TYPE: DNA
<213> ORGANISM: Homo sapiens
<220> FEATURE:
<221> NAME/KEY: unsure
<222> LOCATION: (27)..(68)
<223> OTHER INFORMATION: N is a or g or c or t
<221> NAME/KEY: unsure
<222> LOCATION: (923)
<223> OTHER INFORMATION: R is g or a
<221> NAME/KEY: unsure
<222> LOCATION: (2315)
<223> OTHER INFORMATION: S is g or c

<400> SEQUENCE: 12
cgaattcgcg ggcgcgtcga ccgcggnccc agctcgggag acatgggggg cgttaaagct     60
ctcgtggnat tatccttcag tggggstatt ggactgactt ttcttatgct gggatgtgcc    120
```

-continued

```
ttagaggatt atggatttgg cagttcaccc tgaccatctt gaaaataagt tatctctgat      180
ctctgtctgt atgttacttc tctcccctca ccaacggaga acaaatgtgg gcaaagtgta      240
cttctctgaa gtaagatgat ttgtcaaaaa ttctgtgtgg ttttgttaca ttgggaattt      300
atttatgtga taactgcgtt taacttgtca tatccaatta ctccttggag atttaagttg      360
tcttgcatgc caccaaattc aacctatgac tacttccttt tgcctgctgg actctcaaag      420
aatacttcaa attcgaatgg acattatgag acagctgttg aacctaagtt taattcaagt      480
ggtactcact tttctaactt atccaaaaca actttccact gttgctttcg gagtgagcaa      540
gatagaaact gctccttatg tgcagacaac attgaaggaa ggacatttgt ttcaacagta      600
aattctttag tttttcaaca aatagatgca aactggaaca tacagtgctg gctaaaagga      660
gacttaaaat tattcatctg ttatgtggag tcattattta agaatctatt caggaattat      720
aactataagg tccatctttt atatgttctg cctgaagtgt tagaagattc acctctggtt      780
ccccaaaaag gcagttttca gatggttcac tgcaattgca gtgttcatga atgttgtgaa      840
tgtcttgtgc ctgtgccaac agccaaactc aacgacactc tccttatgtg tttgaaaatc      900
acatctggtg gagtaatttt ccrgtcacct ctaatgtcag ttcagcccat aaatatggtg      960
aagcctgatc caccattagg tttgcatatg gaaatcacag atgatggtaa tttaaagatt     1020
tcttggtcca gcccaccatt ggtaccattt ccacttcaat atcaagtgaa atattcagag     1080
aattctacaa cagttatcag agaagctgac aagattgtct cagctacatc cctgctagta     1140
gacagtatac ttcctgggtc ttcgtatgag gttcaggtga ggggcaagag actggatggc     1200
ccaggaatct ggagtgactg gagtactcct cgtgtcttta ccacacaaga tgtcatatac     1260
tttccaccta aaattctgac aagtgttggg tctaatgttt cttttcactg catctataag     1320
aaggaaaaca agattgttcc ctcaaaagag attgtttggt ggatgaattt agctgagaaa     1380
attcctcaaa gccagtatga tgttgtgagt gatcatgtta gcaaagttac ttttttcaat     1440
ctgaatgaaa ccaaacctcg aggaaagttt acctatgatg cagtgtactg ctgcaatgaa     1500
catgaatgcc atcatcgcta tgctgaatta tatgtgattg atgtcaatat caatatctca     1560
tgtgaaactg atgggtactt aactaaaatg acttgcagat ggtcaaccag tacaatccag     1620
tcacttgcgg aaagcacttt gcaattgagg tatcatagga gcagccttta ctgttctgat     1680
attccatcta ttcatcccat atctgagccc aaagattgct atttgcagag tgatggtttt     1740
tatgaatgca tttttccagcc aatcttccta ttatctggct acacaatgtg gattaggatc     1800
aatcactctc taggttcact tgactctcca ccaacatgtg tccttcctga ttctgtggtg     1860
aagccactgc ctccatccag tgtgaaagca gaaattacta taaacattgg attattgaaa     1920
atatcttggg aaaagccagt cttttccgag aataaccttc aattccagat tcgctatggt     1980
ttaagtggaa agaagtaca atggaagatg tatgaggttt atgatccaaa accaaaatct     2040
gtcagtctcc cagttccaga cttgtgtgca gtctatgctg ttcaggtggc gtttaagagg     2100
ctagatggac tgggatattg gagtaattgg agcaatccag cctacacagt tgtcatggat     2160
ataaaagttc ctatgagagg acctgaattt tggagaataa ttaatggaga tactatgaaa     2220
aaggagaaaa atgtcacttt actttggaag cccctgatga aaaatgactc attgtgcagt     2280
gttcagagat atgtgataaa ccatcatact tcctscaatg gaacatggtc agaagatgtg     2340
ggaaatcaca cgaaattcac tttcctgtgg acagagcaag cacatactgt tacgcttctg     2400
gccatcaatt caattggtgc ttctgttgca aattttaatt taaccttttc atggcctatg     2460
agcaaagtaa atatcgtgca gtcactcagt gcttatcctt taaacagcag ttgtgtgatt     2520
```

```
gtttcctgga tactatcacc cagtgattac aagctaatgt attttattat tgagtggaaa   2580
aatcttaatg aagatggtga aataaaatgg cttagaatct cttcatctgt taagaagtat   2640
tatatccatg atcattttat ccccattgag aagtaccagt tcagtcttta cccaatattt   2700
atggaaggag tgggaaaacc aaagataatt aatagtttca ctcaagatga tattgaaaaa   2760
caccagagtg atgcaggttt atatgtaatt gtgccagtaa ttatttcctc ttccatctta   2820
ttgcttggaa cattattaat atcacaccaa agaatgaaaa agctattttg ggaagatgtt   2880
ccgaacccca agaattgttc ctgggcacaa ggacttaatt ttcagaagag aacggacatt   2940
ctttgaagtc taatcatgat cactacagat gaacccaatg tgccaacttc caacagtct    3000 atagagtatt agaagatttt tacattttga agaaggggag caaatctaaa aaaaattcag   3060
ttgaacttct gagagttaac atatggtgga ttatgttgat ttagaactta aaatagatgt   3120
catttaaacc caagttttac atctaaactc aggtcaaacc tacacactaa ttaaaagttt   3180
agtagatttc aaattttcat cataagtact aaagaccgaa aactaaacag tataaggacc   3240
agtattttgt aattctttta ataccgacaa cgacagtaat gtatagataa tttacagtag   3300
tttatacatc atctgttagg acattaatcc acttgagatt ttgacgttgt agactgttta   3360
tcgaaatttt tatgttacta atattcatac cttagtcact tttataaatc aaacataaaa   3420
atacaggttt gaaaaggtaa aatctaagga aatatctgtg cagtcggatt tttagtcgga   3480
taagcccaca agaaaactta tagaggaccg taaaaacata gattgaaaca gttagaccc    3540 ttaaagtcaa aagttatagg aacttttacc gaattcacta ttgaaggcaa agtcaatttt   3600
ccttcgggct tcaacacaaa cacgacgggt gtcctgtcac cctcaatgtc aagtatagtc   3660
ctactgggat gtatgggtcc agtctaactg ccctggtctt cccttgtagc tgaagattac   3720
aggtgcgaaa gaacaaatta atactggatt tagattaaat gaaggtgact tggtaggttc   3780
tggagaccgt ccgtcccttt acccgtcact asgtttttc cctctgagaa acctcgaaaa   3840
tacttatcaa gtaccactcc tgtcttgaaa agatgaaagt ctgtctgacg aacgatcaaa   3900
atacttaag                                                          3909
```

<210> SEQ ID NO 13
<211> LENGTH: 896
<212> TYPE: PRT
<213> ORGANISM: Homo sapiens
<220> FEATURE:
<221> NAME/KEY: UNSURE
<222> LOCATION: (223)
<223> OTHER INFORMATION: Xaa is unknown or other.
<221> NAME/KEY: UNSURE
<222> LOCATION: (687)
<223> OTHER INFORMATION: Xaa is unknown or other.

<400> SEQUENCE: 13

```
Met Ile Cys Gly Lys Phe Cys Val Val Leu Leu His Trp Gln Phe Ile
 1               5                  10                  15

Tyr Val Ile Thr Ala Phe Asn Leu Ser Tyr Pro Ile Thr Pro Trp Arg
                20                  25                  30

Phe Lys Leu Ser Cys Met Pro Pro Asn Ser Thr Thr Asn Tyr Phe Leu
            35                  40                  45

Leu Pro Ala Gly Leu Ser Lys Asn Thr Ser Asn Ser Asn Gly His Tyr
        50                  55                  60

Glu Thr Ala Val Glu Pro Lys Phe Asn Ser Ser Gly Thr His Phe Ser
    65                  70                  75                  80
```

-continued

```
Asn Leu Ser Lys Thr Thr Phe His Cys Cys Phe Arg Ser Glu Gln Asp
                85                  90                  95
Arg Asn Cys Ser Leu Cys Ala Asp Asn Ile Glu Gly Arg Thr Phe Val
            100                 105                 110
Ser Thr Val Asn Ser Leu Val Phe Gln Gln Ile Asp Ala Asn Trp Asn
        115                 120                 125
Ile Gln Cys Trp Leu Lys Gly Asp Leu Lys Leu Phe Ile Cys Tyr Val
130                 135                 140
Glu Ser Leu Phe Lys Asn Leu Phe Arg Asn Tyr Asn Tyr Lys Val His
145                 150                 155                 160
Leu Leu Tyr Val Leu Pro Glu Val Leu Glu Asp Ser Pro Leu Val Pro
                165                 170                 175
Gln Lys Gly Ser Phe Gln Met Val His Cys Asn Cys Ser Val His Glu
            180                 185                 190
Cys Cys Glu Cys Leu Val Pro Val Pro Thr Ala Lys Leu Asn Asp Thr
        195                 200                 205
Leu Leu Met Cys Leu Lys Ile Thr Ser Gly Val Ile Phe Xaa Ser
210                 215                 220
Pro Leu Met Ser Val Gln Pro Ile Asn Met Val Lys Pro Asp Pro Pro
225                 230                 235                 240
Leu Gly Leu His Met Glu Ile Thr Asp Asp Gly Asn Leu Lys Ile Ser
                245                 250                 255
Trp Ser Ser Pro Leu Val Pro Phe Pro Leu Gln Tyr Gln Val Lys
            260                 265                 270
Tyr Ser Glu Asn Ser Thr Thr Val Ile Arg Glu Ala Asp Lys Ile Val
        275                 280                 285
Ser Ala Thr Ser Leu Leu Val Asp Ser Ile Leu Pro Gly Ser Ser Tyr
290                 295                 300
Glu Val Gln Val Arg Gly Lys Arg Leu Asp Gly Pro Gly Ile Trp Ser
305                 310                 315                 320
Asp Trp Ser Thr Pro Arg Val Phe Thr Thr Gln Asp Val Ile Tyr Phe
                325                 330                 335
Pro Pro Lys Ile Leu Thr Ser Val Gly Ser Asn Val Ser Phe His Cys
            340                 345                 350
Ile Tyr Lys Lys Glu Asn Lys Ile Val Pro Ser Lys Glu Ile Val Trp
        355                 360                 365
Trp His Asn Leu Ala Glu Leu Ile Pro Gln Ser Gln Tyr Asp Val Val
370                 375                 380
Ser Asp His Val Ser Lys Val Thr Phe Phe Asn Leu Asn Glu Thr Lys
385                 390                 395                 400
Pro Arg Gly Leu Phe Thr Tyr Asp Ala Val Tyr Cys Cys Asn Glu His
                405                 410                 415
Gly Cys His His Arg Tyr Ala Gly Leu Tyr Val Ile Asn Val Asn Ile
            420                 425                 430
Asn Ile Ser Cys Gln Thr Asn Gly Tyr Leu Thr Lys Met Thr Cys Arg
        435                 440                 445
Trp Ser Thr Ser Thr Ile Gln Ser Leu Ala Glu Ser Thr Leu Glu Leu
450                 455                 460
Arg Tyr His Arg Ser Ser Leu Tyr Cys Ser Asn Ile Pro Ser Ile His
465                 470                 475                 480
Pro Ile Ser Glu Pro Lys Asn Cys Tyr Leu Gln Ser Asn Gly Phe Tyr
                485                 490                 495
Gln Cys Ile Pro Gln Pro Ile Phe Leu Leu Ser Gly Tyr Thr Met Trp
```

```
                    500                 505                 510
Ile Arg Ile Asn His Ser Leu Gly Ser Leu Asn Ser Pro Pro Thr Cys
            515                 520                 525

Val Leu Pro Asp Ser Val Val Lys Pro Leu Pro Pro Ser Ser Val Lys
530                 535                 540

Ala Glu Ile Thr Ile Asn Ile Gly Leu Leu Lys Ile Ser Trp Glu Lys
545                 550                 555                 560

Pro Val Phe Pro Glu Asn Asn Leu Gln Phe Gln Ile Arg Thr Gly Leu
                565                 570                 575

Ser Gly Lys Glu Val Gln Trp Lys Met Tyr Glu Val Thr Asn Pro Lys
            580                 585                 590

Pro Lys Ser Val Ser Leu Pro Val Pro Asp Leu Cys Ala Val Tyr Ala
        595                 600                 605

Val Gln Val Arg Phe Lys Arg Leu Asp Gly Leu Gly Tyr Trp Ser Asn
610                 615                 620

Trp Ser Asn Pro Ala Tyr Thr Val Val Met Asp Ile Lys Val Pro Met
625                 630                 635                 640

Arg Gly Pro Glu Phe Trp Arg Ile Ile Asn Gly Asp Thr Met Lys Lys
                645                 650                 655

Glu Lys Asn Val Tyr Leu Leu Trp Lys Pro Leu Met Lys Asn Asp Ser
            660                 665                 670

Leu Cys Ser Val Gln Arg Tyr Val Ile Asn His His Thr Ser Xaa Asn
        675                 680                 685

Gly Thr Trp Ser Glu Asn Val Gly Asn His Thr Lys Phe Thr Phe Leu
    690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
                725                 730                 735

Lys Val Asn Ile Val Gln Ser Leu Ser Ala Tyr Pro Leu Asn Ser Ser
            740                 745                 750

Cys Val Ile Val Ser Trp Ile Leu Ser Pro Ser Asp Val Lys Leu Met
        755                 760                 765

Tyr Pro Ile Ile Glu Trp Lys Asn Leu Asn Glu Asp Gly Glu Ile Lys
770                 775                 780

Trp Leu Arg Ile Ser Ser Ser Val Lys Lys Tyr Tyr Ile His Asp His
785                 790                 795                 800

Phe Ile Pro Ile Glu Lys Tyr Gln Phe Ser Leu Tyr Pro Ile Phe Met
                805                 810                 815

Glu Gly Val Gly Lys Pro Lys Ile Ile Asn Ser Phe Thr Gln Asn Asn
            820                 825                 830

Ile Glu Lys His Gln Ser Asp Ala Gly Leu Tyr Val Ile Val Pro Val
        835                 840                 845

Ile Ile Ser Ser Ser Ile Leu Leu Leu Gly Thr Leu Leu Ile Ser His
850                 855                 860

Gln Arg Met Lys Lys Leu Phe Trp Glu Asp Val Pro Asn Pro Lys Asn
865                 870                 875                 880

Cys Ser Trp Ala Gln Gly Leu Asn Phe Gln Lys Arg Thr Asn Ile Leu
                885                 890                 895

<210> SEQ ID NO 14
<211> LENGTH: 30
<212> TYPE: PRT
<213> ORGANISM: Artificial Sequence
```

<220> FEATURE:
<223> OTHER INFORMATION: Description of Artificial Sequence:Synthetic

<400> SEQUENCE: 14

Met Val Leu Ala Ser Ser Thr Thr Ser Ile His Thr Met Leu Leu Leu
 1               5                  10                  15

Leu Leu Met Leu Pro His Leu Gly Leu Gly Ala Ser Ile Ser
            20                  25                  30

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence:Synthetic

<400> SEQUENCE: 15

Ala Thr Leu Ala Ala Ala Ala Leu
 1               5

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 16 attgggtaa gttatt                                              16

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 17
aaataggtaa gcatta                                             16

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 18
tgttctgtaa gtacca                                             16

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 19
cacaaggtag gttatg                                             16

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence:Synthetic

```
<400> SEQUENCE: 20
tgattggtaa gaaaca                                                   16

<210> SEQ ID NO 21
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 21
attgaggtat catagg                                                   16

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 22
ctgtgggtat gtcaag                                                   16

<210> SEQ ID NO 23
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 23
tggaaggtac cttta                                                    16

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 24
taaaaggtct gcagag                                                   16

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence:Synthetic
<221> NAME/KEY: unsure
<222> LOCATION: (11)
<223> OTHER INFORMATION: N is a or g or c or t

<400> SEQUENCE: 25
tggagggtat nccaat                                                   16

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 26
caattcaatt ggtgct                                                   16
```

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 27
ccaaaggtat tgtact    16

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 28
cataaggttg cttttt    16

<210> SEQ ID NO 29
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 29
ccttttccag gtgtat    16

<210> SEQ ID NO 30
<211> LENGTH: 15
<212> TYPE: DNA
<213> ORGANISM: Artificial Sequence
<220> FEATURE:
<223> OTHER INFORMATION: Description of Artificial Sequence:Synthetic

<400> SEQUENCE: 30
tcctaacaga attta    15

<210> SEQ ID NO 31
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 31
ttaaattcag atgcaa    16

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 32
tatttaacag gctgac    16

<210> SEQ ID NO 33
<211> LENGTH: 16
<212> TYPE: DNA
<213> ORGANISM: Artificial Sequence
<220> FEATURE:

<223> OTHER INFORMATION: Description of Artificial Sequence:Synthetic

<400> SEQUENCE: 33
ctcattacag atgtca                                                         16

<210> SEQ ID NO 34
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 34
tttcaaatag atgtga                                                         16

<210> SEQ ID NO 35
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 35
tcttttaaag gagcag                                                         16

<210> SEQ ID NO 36
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 36
aaatttctag tgaagc                                                         16

<210> SEQ ID NO 37
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 37
tattttacag atgtat                                                         16

<210> SEQ ID NO 38
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 38
catttggcag ttccta                                                         16

<210> SEQ ID NO 39
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 39
tttactacag cccctg                                                         16

```
<210> SEQ ID NO 40
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 40 tcttttcag atgata                                                          16

<210> SEQ ID NO 41
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 41
ccctttgtag aatgaa                                                         16

<210> SEQ ID NO 42
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 42
ccttttccag aaaatg                                                         16

<210> SEQ ID NO 43
<211> LENGTH: 16
<212> TYPE: DNA
<213> ORGANISM: Artificial Sequence
<220> FEATURE:
<223> OTHER INFORMATION: Description of Artificial Sequence:Synthetic

<400> SEQUENCE: 43
atctaaacag agaacg                                                         16

<210> SEQ ID NO 44
<211> LENGTH: 32
<212> TYPE: PRT
<213> ORGANISM: Artificial Sequence
<220> FEATURE:
<221> NAME/KEY: UNSURE
<222> LOCATION: (27)
<223> OTHER INFORMATION: Xaa is unknown or other.
<221> NAME/KEY: UNSURE
<222> LOCATION: (31)
<223> OTHER INFORMATION: Xaa is unknown or other.

<400> SEQUENCE: 44

Ala Ser Ile Ser Ser Ser Ala Thr Leu Ala Ala Ala Gly Ser Ala Thr
 1               5                  10                  15

Pro Ile Thr Pro Thr Ala Pro Leu Leu Ser Xaa Met Pro Pro Xaa Ser
             20                  25                  30
```

US 6,414,128 B1

HAEMOPOIETIN RECEPTOR AND GENETIC SEQUENCES ENCODING SAME

BACKGROUND OF THE INVENTION

The preferred haemopoietin receptor of the present invention is referred to herein as "NR2". The NR2 receptor interacts with leptin and is referred to as a "leptin receptor". The terms "haemopoietin receptor", "NR2 and "leptin receptor" are used in interchangeably throughout the subject specification. The species from which a particular NR2 is desired is given in single letter abbreviation in lower case before NR2. For example, murine NR2 is "mNR2" and human NR2 is "hNR2". A recombinant form may have the prefix "r".

The rapidly increasing sophistication of recombinant DNA techniques is greatly facilitating research into the medical and allied health fields. Cytokine research is of particular importance, especially as these molecules regulate the proliferation, differentiation and function of a wide variety of cells. Administration of recombinant cytokines or regulating cytokine function and/or synthesis is becoming increasingly the focus of medical research into the treatment of a range of disease conditions.

Despite the discovery of a range of cytokines and other secreted regulators of cell function, comparatively few cytokines are directly used or targeted in therapeutic regimums. One reason for this is the pleiotropic nature of many cytokines. For example, interleukin (IL)-11 is a functionally pleiotropic molecule (1,2), initially characterized by its ability to stimulate proliferation of the IL-6-dependent plasmacytoma cell line, T11 65 (3). Other biological actions of IL-11 include induction of multipotential haemopoietin progenitor cell proliferation (4,5,6), enhancement of megakaryocyte and platelet formation (7,8,9,10), simulation of acute phase protein synthesis (11) and inhibition of adipocyte lipoprotein lipase activity (12, 13). The diverse and pleiotropic function of IL-11 and other haemopoietin cytokines makes these molecules an important group to study, especially at the level of interaction of the cytokines with their receptors. Manipulation and control of cytokine receptors and of cytokine-receptor interaction is potentially very important in many therapeutic situations, especially where the target cytokine is functionally pleiotropic and it is desired to block certain functions of a target cytokine but not all functions.

Another important aspect of cytokine receptors is in the search for new cytokines. In this regard, the inventors have used a procedure for cloning haemopoietin receptors without prior knowledge of their ligands. Identification of receptors then provides a screening procedure for potentially new cytokines and for previously characterised cytokines. In addition, identification of new haemopoietin receptors allows for selective blocking of pleiotropic cytokine function.

In accordance with the present invention, the inventors identified a novel haempoietin receptor which interacts with leptin, a hormone which regulates adipose tissue mass.

BRIEF SUMMARY OF THE INVENTION

The present invention is directed to a novel haemopoietin receptor or a derivative thereof and to genetic sequences encoding same. The receptor molecule and its derivatives and the genetic sequences encoding same of the present invention are useful in the development of a wide range of agonists, antagonists, therapeutics and diagnostic reagents based on ligand interaction with its receptor. The present invention particularly relates to a receptor for leptin.

BRIEF DESCRIPTION OF THE DRAWINGS

FIGS. 2A to 2K are a representation of the nucleotide sequence and corresponding amino acid sequence of the haemopoietin receptor.

DETAILED DESCRIPTION OF THE INVENTION

Figure 1:
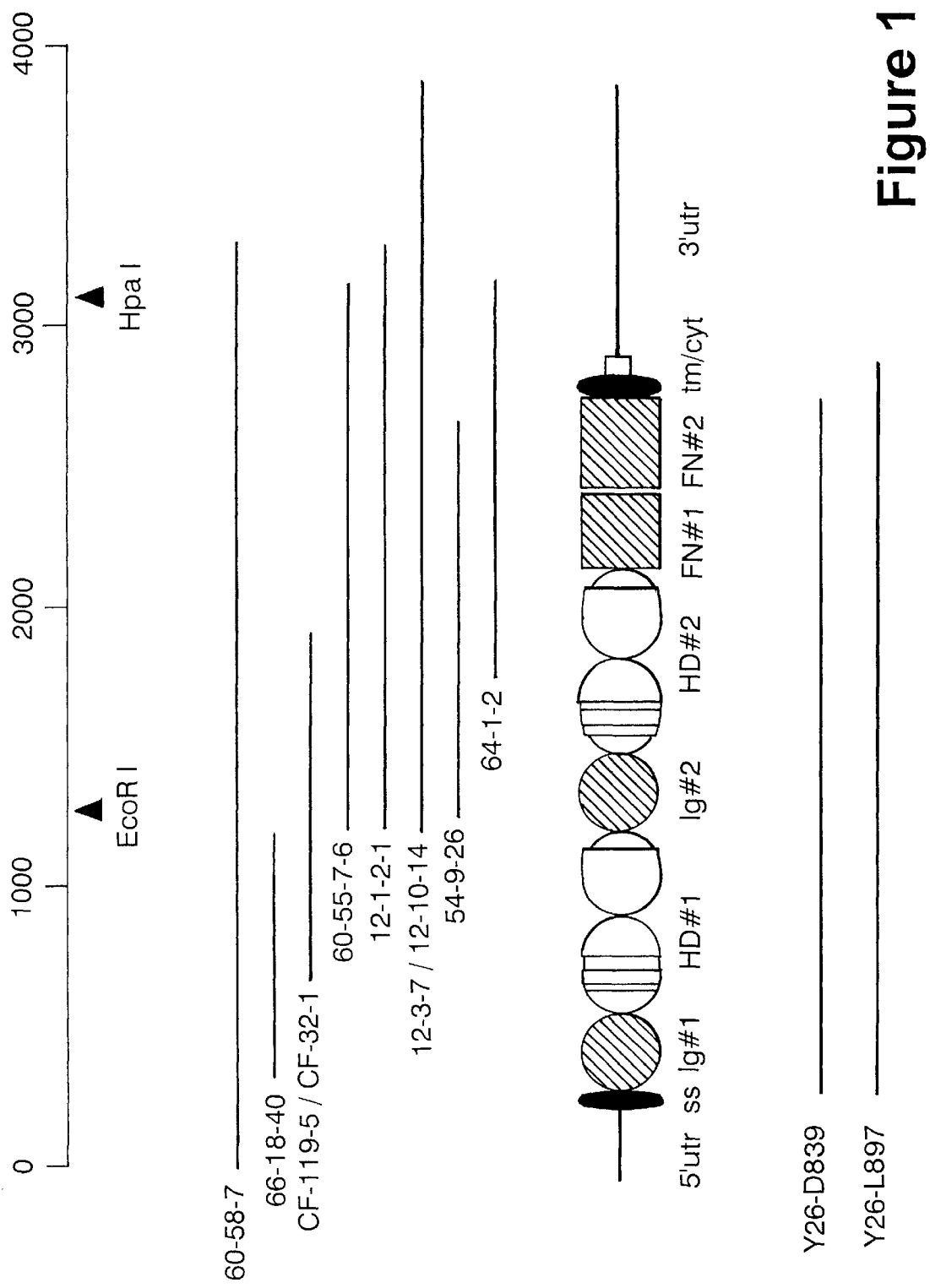
FIG. 1 is a schematic resentation showing size of NR2 cDNA clones isolated and schematic structure of the predicted NR2 protein.
Figure 3A:
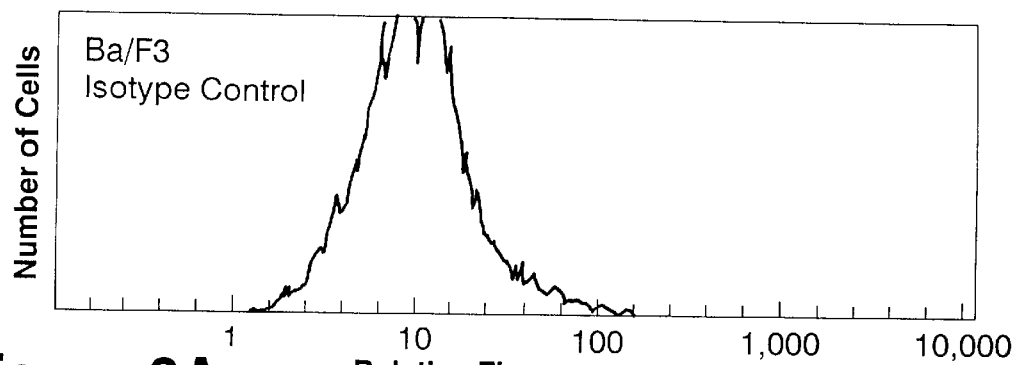
FIG. 3 is a representation of a FACS analysis of NR2 expression by BA/F$_3$ cells.
Figure 3B:
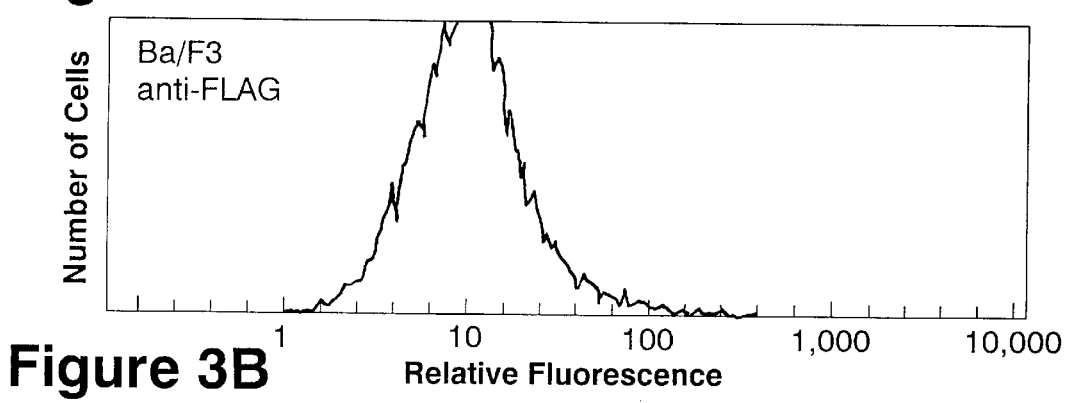
Figure 3C:
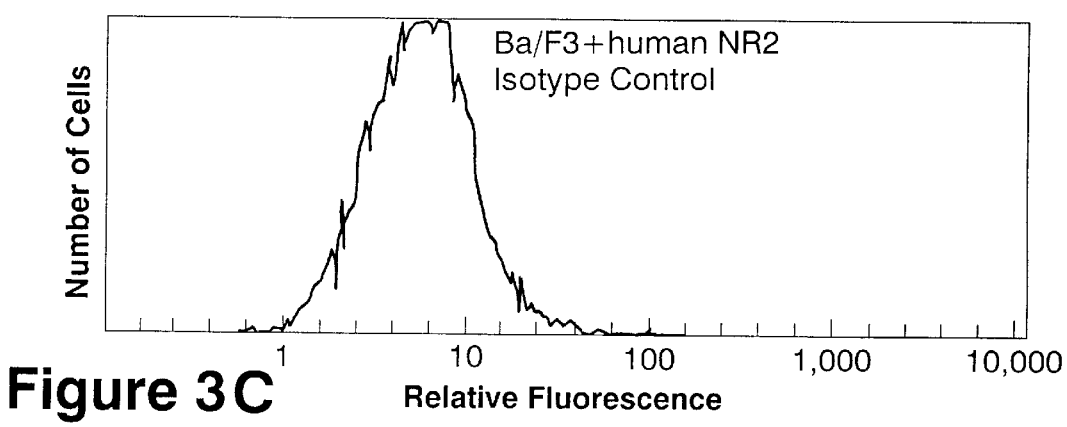
Figure 3D:
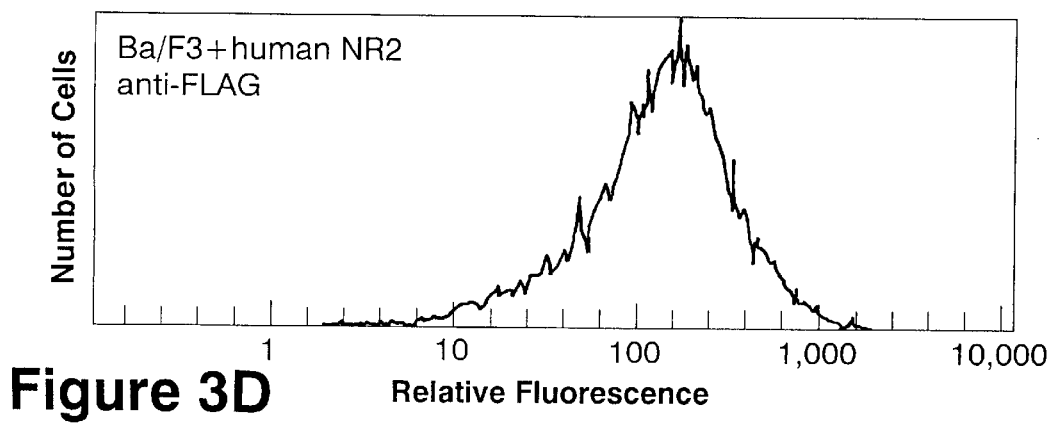

Bibliographic details of the publications numerically referred to in this specification are collected at the end of the description. Sequence Identity Numbers (SEQ ID NOs.) for the nucleotide and amino acid sequences referred to in the specification are defined following the bibliography.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

One aspect of the present invention is directed to an isolated nucleic acid molecule comprising a sequence of nucleotides encoding or complementary to a sequence encoding a haemopoietin receptor or a derivative thereof wherein said sequence of nucleotides or a complamantary form thereof is capable of hybridising under medium stringent conditions to the oligonucleotide:

5'-(A/G)CTCCA(A/G)TC(A/G)CTCCA-3' [SEQ ID NO: 1].

In a preferred embodiment, the nucleic acid molecule comprises a nucleotide sequence or a complementary form thereof which hybridises under medium stringent conditions to the oligonucleotides:

5'-(A/G)CTCCA(A/G)TC(A/G)CTCCA-3' [SEQ ID NO:1]

5'-ACTAGCAGGGATGTAGCTGAG-3' [SEQ ID NO:4]

5'-CTGCTCCTATGATACCT-3'[SEQ ID NO:6]

5'-CCTCTTCCATCTTATTGCTTGG-3' [SEQ ID NO:7]

5'-ATCGGTCGTGACATACAAGG-3'[SEQ ID NO:8].

In an even more preferred embodiment, the nucleic acid molecule comprises a nucleotide sequence or a complementary form thereof which hybridises under medium stringent conditions to one or more of the following oligonucleotides:

5'-(A/G)CTCCA(A/G)TC(A/G)CTCCA-3' [SEQ ID NO: 1].

5'-ACTAGCAGGGATGTAGCTGAG-3' [SEQ ID NO:4]

5'-CTCAGCTACATCCCTGCTAGT-3' [SEQ ID NO:5]

5'-CTGCTCCTATGATACCT-3' (SEQ ED NO:6]

5'-CCTCTTCCATCTTATTGCTTGG-3' [SEQ ID NO:7]

5'-ATCGGTCGTGACATACAAGG-3'[SEQ ID NO:8]

5'-AGCTAAGCTTTCTAGATATCCAATTACTCCTTGGAGA-3' [SEQ ID NO:9]

5'-AGCTTCTAGATCAAACTTTTATATCCATGACAAC-3'[SEQ ID NO:10]

5'-AGCTTCTAGATCAAACTTTTATATCCATGACAAC-3'[SEQ ID NO: 11].

In a still more preferred embodiment, the nucleic acid molecule comprises a nucleotide sequece or complementary form thereof which is capable of hybridising separately under medium stringent conditions to each of oligonucleotide SEQ ED NO:1 and SEQ ID NO:4 to SEQ ID NO:11.

In a most preferred embodiment, the present invention provides a nucleic acid molecule comprising a sequence of nucleotides or a complementary form thereof substantially as set forth in FIG. 2 [SEQ ID NO: 12] or a sequence of nucleotides capable of hybridising to all or part thereof under medium stringent conditions.

Accordingly, a preferred embodiment of the present invention is also directed to a nucleic acid molecule encoding a haemopoietin receptor or a derivative thereof and comprising a nucleotide sequence as set forth in SEQ ID NO:12 or is capable of hybridising to all or part thereof under medium stringent conditions.

The haemopoietin receptor of the present invention is referred to herein as "NR2". In accordance with the present invention, NR2 is capable of interacting with leptin and, hence, is also referred to as a "leptin receptor".

The term "derivative" includes any or all parts, fragments, portions, homologues or analogues to the nucleotide sequence set forth in SEQ ID NO:12 as well as hybrid molecules between the NR2 receptor and other receptors or other molecules. Derivatives include single or multiple nucleotide substitutions, deletions and/or additions to the nucleotide sequence set forth in SEQ ID NO:12.

Another aspect of the present invention contemplates a recombinant haemopoietin receptor encoded by the nucleic acid molecules as hereinbefore described.

According to one aspect of this embodiment, there is provided recombinant haemopoietin receptor encoded by a nucleic acid molecule which comprises a nucleotide sequence or a complementary form thereof which is capable of hybridising to SEQ ID NO:1 under medium stringent conditions.

In a preferred embodiment, the recombinant haemopoietin receptor is encoded by a nucleic acid molecule which comprises a nucleotide sequence or a complementary form thereof which is capable of hybridising to SEQ ID NO:1, SEQ ID NO:4, SEQ ID NO:6, SEQ ID NO:7 and SEQ ID NO:8 under medium strent conditions.

In an even more preferred embodiment, the recombinant haemopoietin receptor is encoded by a nucleic acid molecule which comprises a nucleotide sequence or complementary form thereof which hybridises under medium stringency conditions to one or more of SEQ ID NO:1 and SEQ ID NO:4 to SEQ ID NO:11.

In still an even more preferred embodiment, the recombinant haemopoietin receptor is encoded by a nucleic acid molecule which comprises a nucleotide sequence or a complementary form thereof which hybridises under medium stringent conditions to each of oligonucleotides SEQ ID NO:1 and SEQ ID NO:4 to SEQ ID NO:11.

In a most preferred embodiment, the present invention is directed to a recombinant NR2 encoded by a nucleic acid molecule comprising a nucleotide sequence or complementary form thereof substantially as set forth in SEQ ID NO:12 or a sequence capable of hybridising to all or part thereof under medium stringent conditions.

According to this latter aspect of the present invention, there is provided a recombinant NR2 having an amino acid sequence subantially as set forth in FIG. 2 [SEQ ID NO:13] or having at least about 60% similarity to all or part thereof, more preferably at least about 70%, still more preferably at least about 80% and still more preferably at least about 90–95% or above (e.g. 96%, 97%, 98% or greater than or equal to 99%) similarly to all or part of the amino acid sequence set forth in SEQ ID NO:13.

The recombinant NR2 or a genetic sequence encoding same is preferably in isolated form meaning that a composition of matter comprises at least about 10%, more preferably at least about 20%, still more preferably at least about 30–40%, even more preferably at least about 50–60%, still even more preferably at least about 70–80% or greater (e.g. 85%, 90or 95%) of the recombinant receptor or genetic sequence encoding same relative to other components in the composition as determined by, for example, molecular weight, activity, nucleic acid content or composition or other convenient means.

Reference herein to "recombinant haemopoietin receptor", "NR2" or "leptin receptor" includes reference to derivatives thereof such as parts, fragments, portions, homologues, hybrids or analogues thereof. The derivatives may be finctional or not or may be non-functional but immunologically interactive with antibodies to all or part of the receptor. Derivatives of the receptor also cover agonists or antagonists of receptor-ligand interaction. Function is conveniently defined by an ability of NR2 to interact with leptin or for soluble NR2 to compete with leptin-induced activities of certain cells.

For the purposes of defining the level of stringency, reference can conveniently be made to Sambrook et al (14) which is herein incorporated by reference where the washing steps disclosed at pages 952-957 are considered high stringency. A low stringency is defined herein as being in 4-6X SSC/0.1–0.5% w/v SDS at 37–45° C. for 2–3 hours. Depending on the source and concentration of nucleic acid involved in the hybridisation, alternative conditions of stringency may be employed such as medium stringent conditions which are considered herein to be 1–4X SSC/0.25–0.5% w/v SDS at $\geq$ 45° C. for 2–3 hours or high stringent conditions considered herein to be 0.1–1X SSC/0.1% w/v SDS at $\geq$60° C. for 1–3 hours.

The nucleic acid molecule is preferably derivable from the human genome but genomes and nucleotide sequences from non-human animals are also encompassed by the present invention. Non-human animals contemplated by the present invention include livestock animals (e.g. sheep, cows, pigs, goats, horses, donkeys), laboratory test animals (e.g. mice, rats, guinea pigs, hamsters, rabbits), domestic companion animals (e.g. dogs, cats), birds (e.g. chickens, geese, ducks and other poultry birds, game birds, emus, ossriches) and captive wild or tamed animals (e.g. foxes, kangaroos, dingoes).

Preferred human genetic sequences encoding NR2 include sequences from cells of bone marrow, brain, liver, kidney, heart, testis, stomach, lymph nodes, colon, spleen and ovary, neonatal tissue, embryonic tissue, cancer or tumour-derived tissues.

The nucleic acid molecule of the present invention may be single or double stranded, linear or closed circle DNA (e.g. genomic DNA), cDNA or mRNA or combinations thereof such as in the form of DNA:RNA hybrids. The nucleic acid molecule may also include a vector such as an expression vector component to facilitate expression of the haemopoietin recetor or its components or parts.

As stated above, the present invention further contemplates a range of derivatives of NR2. Derivatives include fragments, parts, portions, mutants, homologues and analogues of the NR2 polypeptide and corresponding genetic sequence. Derivatives also include single or multiple amino acid substitutions, deletions and/or additions to NR2 or single or multiple nucleotide substitutions, deletions and/or additions to the genetic sequence encoding NR2. "Additions" to amino acid sequences or nucleotide sequences include fusions with other peptides, polypeptides or proteins or fusions to nucleotide sequences. Reference herein to "NR2" includes reference to all derivatives thereof including functional derivatives or "NR2" immunologically interactive derivatives.

Analogues of NR2 contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecule or their analogues.

Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2, 4, 6trinitrobenzene sulphonic acid (TNBS); acylation of amino groups with succinic anhydride and tetrahydrophthalic anhydride; and pyridoxylation of lysine with pyridoxal-5- phosphate followed by reduction with NaBH4.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitision, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4- chloromercuriphenylsulphonic acid, phenylmercury chloride, 2-choloromercuri-4-nitrophenol and other mercurials; carbamoylation with cyanate at akaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoactic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5- phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D- isomers of amino acids. A list of unnatural amino acid, contemplated herein is shown in Table 1.

Crosslinkers can be used, for example, to stabilise 3D conformations, using horno-bifunctional crosslinkers such as the bifunctional imido esters havig $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond bethween the N and C termini between two side chains or between a side chain and the N or C terminus.

These types of modifications may be important to stabilise NR2 if administered to an individual or for use as a diagnostic reagent.

The present invention further contemplates chemical analogues of NR2 capable of acting as antagonists or agonists of NR2 or which can act as functional analogues of NR2. Chemical analogues may not necessarily be derived from NR2 but may share certain conformational similarities. Alternatively, chemical analogues may be specifically designed to mimic certain physiochemical properties of NR2. Chemical analogues may be chemically synthesised or may be detected following, for example, natural product screening.

The idenification of NR2 permits the generation of a range of therapeutic molecules capable of modulating expression of NR2 or modulating the activity of NR2. Modulators contemplated by the present invention includes agonists and antagonists of NR2 expresion. Antagonists of NR2 expression include antisense molecules, ribozymes and co-suppression molecules. Agonists include molecules which increase promoter ability or interfere with negative regulatory mechanisms. Agonists of NR2 include molecules which overcome any negative regulatory mechanism. Antagonists of NR2 include antibodies and inhibitor peptide fragmets.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-amiobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-a-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydrodxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalamine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl))glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |

TABLE 1-continued

| Non-conventional amino acid | Code | Non-conventional amino acid | Code |
|---|---|---|---|
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

Other derivatives contemplated by the present invention include a range of glycosylation variants from a completely unglycosylated molecule to a modified glycosylated molecule. Altered glycosylation patterns may result from expression of recombinant molecules in different host cells.

Another embodiment of the present invention contemplates a method for modulating expression of NR2 in a human, said method comprising contacting the NR2 gene encoding NR2 with an effective amount of a modulator ofNR2 exepression for a time and under conditions sufficient to up-regulate or down-regulate or otherwise modulate expression ofNR2. For example, a nucleic acid molecule encoding NR2 or a derivative thereof may be introduced into a cell to enhance NR2 related activities of that cell. Conversely, NR2 antisense sequences (or sense sequences for co-suppression) such as oligonucleotides may be introduced to decrease NR2-related activies of any cell expressing the endogenous NR2 gene. Ribozymes may also be used.

Another aspect of the present invention contemplates a method of modulating an activiy of NR2 in a human, said method comprising administering to said mammal a modulating effective amount of a molecule for a time and under conditions sufficient to increase or decrease NR2 activity. The molecule may be a proteinaceous molecule or a chemical entity and may also be a derivative of NR2 or its receptor or a chemical analogue or truncation mutant of NR2 or its receptor.

Accordingly, the present invention contemplates a pharmaceutical composition comprising NR2 or a derivative thereof or a modulator of NR2 expression or NR2 activity and one or more pharmaceutically acceptable carriers and/or diluents. These components are referred to as the [active ingredients[].

In this regard there is provided a pharmaceutical composition comprising a recombinant haemopoietin recpter as hereinbefore decribed or a ligand (e.g. leptin) binding portion thereof and one or more pharmaceutically acceptable carrers and/or diluents.

In another embodiment, there is provided a pharmaceutical composition comprising a ligand (e.g. leptin) to the recombinant haemopoietin receptor as hereinbefore described and one or more pbarmaceutically acceptable carriers and/or diluents.

Still a further aspect of the present invention contemplates a method of treatment of an animal comprising administering to said animal a treatment effective amount of a recombinant haemopoietin receptor as hereinbefore described or a ligand binding portion thereof or a ligand (e.g. leptin) to said haempoietic receptor for a time and under conditions sufficient for said treatment to be substantially effected or the conditions to be substantially ameliorated.

The pharmaceutical forms suitable for injectable use include sterile aqueous solutions (where water soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained for example, by the use of a coating such as licithin, by the maintenance of the required particle size in the case of dispersion and by the use of superfactants. The preventions of the action of microorganisms can be brought about by various antbacterial and antifungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepaed by incorporating the active compounds in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 ug and 2000 mg of active compound.

The tablets, troches, pills, capsules and the like may also contain the components as listed hereafter: A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materis may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The present invention also extends to forms suitable for topical application such as creams, lotions and gels.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingrdients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the reqired pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 $\mu$g to about 2000 mg. Expressed in proportions, the active compound is generally present in from about 0.5 $\mu$g to about 2000 mg/ml of carrier. In the case of compositions containing supplementary active ingredients, the dosages are determined by reference to the usual dose and manner of administration of the said ingredients.

The pharmaceutical composition may also comprise genetic molecules such as a vector capable of transfecting target cells where the vector carries a nucleic acid molecule capable of modulating NR2 expression or NR2 activity. The vector may, for example, be a viral vector.

Still another aspect of the present invention is directed to antibodies to NR2 and its derivatives or its ligands (e.g. leptin). Such antibodies may be monoclonal or polyclonal and may be selected from naturlly occurring antibodies to NR2 or may be specifically raised to NR2 or derivatives thereof. In the case of the latter, NR2 or its derivatives may first need to be associated with a carrier molecule. The antibodies and/or recombinant NR2 or its derivatives of the present invention are particularly useful as therapeutic or diagnostic agents.

For example, NR2 and its derivatives can be used to screen for naturally occurring antibodies to NR2. These may occur, for example in some autoimmune diseases. Alternatively, specific antibodies can be used to screen for NR2. Techniques for such assays are well known in the art and include, for examnple, sandwich assays and ELISA. Knowledge ofNR2 levels may be important for diagnosis of certain cancers or a predisposition to cancers or for monitoring certain therapeutic protocols.

Antibodies to NR2 of the present invention may be monoclonal or polyclonal. Alternatively, fragments of antibodies may be used such as Fab fragments. Furethermore, the present invention extends to recombinant and synthetic antibodies and to antibody hybrids. A "synthetic antibody" is considered herein to include fragments and hybrids of antibodies. The antibodies of this aspect of the present invention are particularly useful for immunotherapy and may also be used as a diagnostic tool for assessing the receptor or receptor-ligand interaction or monitoring the program of a therapeutic regimin.

For example, specific antibodies can be used to screen for NR2 proteins. The latter would be important, for example, as a means for screening for levels of NR2 in a cell extract or other biological fluid or purifying NR2 made by recombinant means from culture supernatant fluid. Techniques for the assays contemplated herein are known in the art and include, for example, sandwich assays and ELISA.

It is within the scope of this invention to include any second antibodies (monoclonal, polyclonal or fragments of antibodies or synthetic antibodies) directed to the first mentioned antibodies discussed above. Both the first and second antibodies may be used in detection assays or a first antibody may be used with a commercially available anti-immunoglobulin antibody. An antibody as contemplated herein includes any antibody specific to any region of NR2.

Both polyclonal and monoclonal antibodies are obtainable by immunization with the enzyme or protein and either type is utilizable for immunoassays. The methods of obtaining both types of sera are well known in the art. Polyclonal sera are less preferred but are relatively easily prepared by injection of a suitable laboratory animal with an effective amount of NR2, or antigenic parts thereof, collecting serum from the animal, and isolating specific sera by any of the known immunoadsorbent techniques. Although antibodies produced by this method are utilizable in virtally any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Another aspect of the present invention contemplates a method for detecting NR2 in a biological sample from a subject said method comprising contacting said biological sample with an antibody specific for NR2 or its derivatives or homologues for a time and under conditions sufficient for an antibody-NR2 complex to form, and then detecting said complex.

The presence of NR2 may be accomplished in a number of ways such as by Western blotting and ELISA procedures. A wide range of immunoassay techniques are available as can be seen by reference to U.S. Pat. Nos. 4,016,043, 4,424,279 and 4,018,653. These, of course, includes both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwhich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent. In accordance with the present invention the sample is one which might contain NR2 including cell extract, tissue biopsy or possibly serum, saliva, mucosal secretions, lymph, tissue fluid and respiratory fluid. The sample is, therefore, generally a biological sample comprising a biological fluid, cell extract, bone marrow or lymph, tissue extract (e.g. from kidney, liver, spleen, etc), fermentation fluid and supernatant fluid such as from a cell culture and cell conditioned medium.

In the typical forward sandwich assay, a first antibody having specificity for the NR2 or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes) and under suitable conditions (e.g. 25° C.) to allow binding of any subunit present in the antibody. Following the incubation period, the antibody subunit solid phase is washed and dried and incubated with a second antibody specific for a portion of the hapten. The second antibody is linked to a reporter molecule which is used to indicate the binding of the second antibody to the hapten.

An alternative method involves immobilizhng the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules. In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrte is then added to the complex of antibody-antigen-antibody. The substrate will react with the enzyme linked to the second antibody, giving a qualitative visual signal, which may be furter quantitated, usually spectrophotometrically, to give an indication of the amount of hapten which was present in the sample. "Reporter molecule" also extends to use of cell agglutination or inhibition of agglutination such as red blood cells on latex beads, and the like.

Alternatively, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest Immunofluorescene and EIA techniques are both very well established in the art and are particularly preferred for the present method. However, other reporter molecules, such as radioisotope, chemiluminescent or bioluminescent molecules, may also be employed.

The present invention also contemplates genetic assays such as involving PCR analysis to detect NR2 gene or its derivatives. Alternative methods or methods used in conjunction include direct nucleotide sequencing or mutation scanning such as single stranded conformation polymorphoms analysis (SSCP) as specific oligonucleotide hybridisation, as methods such as direct protein truncation tests. Such genetic tests may be important, for example, in genetic screening of animals (e.g. humans) for non-expression or substantial absence of expression or expression of mutant forms of NR2 leading to conditions such as obesity or other effects of leptin-receptor interaction.

The nucleic acid molecules of the present invention may be DNA or RNA. When the nucleic acid molecule is in DNA form, it may be genomic DNA or cDNA. RNA forms of the nucleic acid molecules of the present invention are generally mRNA.

Although the nucleic acid molecules of the present invention are generally in isolated form, they may be integrated into or ligated to or otherwise fused or associated with other genetic molecules such as vector molecules and in particular expression vector molecules. Vectors and expression vectors are generally capable of replication and, if applicable, expression in one or both of a proklyotic cell or a eukaryotic cell. Preferably, prokaryotic cells include *E. Col. Bacillus sp* and *Pseudomonas sp*. Preferred eukaryotic cells include yeast, fungal, mammalian and insect cells.

Accordingly, another aspect of the present invention contemplates a genetic construct comprising a vector portion and a mammalian and more particularly a human NR2 gene portion, which NR2 gene portion is capable of encoding an NR2 polypeptide or a functional or immunologically interactive derivative thereof.

Preferably, the NR2 gene portion of the genetic construct is operably linked to a promoter on the vector such that said promoter is capable of directing expression of said NR2 gene portion in an appropriate cell.

In addition, the NR2 gene portion of the genetic consruct may comprise all or part of the gene fused to another genetic sequence such as a nucleotide sequence encoding glutathione-S- transferase or part thereof or a cytokine or another haempoietic receptor. Hybrid receptor molecules are particularly useful in the development of multi functional therapeutic and diagnostic agents.

The present invention extends to such genetic constructs and to prokaryotic or eukaryotic cells comprising same.

The present invention also extends to any or all derivatives of NR2 including mutants, part, fragments, portions, homologues and analogues or their encoding genetic sequence including single or multiple nucleotide or amino acid substitutions, additions and/or deletions to the naturally occurring nucleotide or amino acid sequence.

The NR2 and its genetic sequence of the present invention will be useful in the generation of a range of therapeutic and diagnostic reagents and will be especially useful in the detection of a correponding ligand. For example, recombinant NR2 may be bound or fused to a reporter molecule capable of producing an identifiable signal, contacted with a biological sample putatively containing a ligand and screening for binding of the labelled NR2 to the ligand. Alternatively, labelled NR2 may be used to screen expression libraries of putative ligand genes or functional parts thereof.

In another embodiment, the NR2 is first immobilised. According to this embodiment, there is provided a method comprising contacting a biological sample containing a putative ligand with said haempoietic receptor or a ligand binding portion thereof immobilised to a solid support for a time and under conditions sufficient for a complex to form between said receptor and said ligand if said ligand is present in said biological sample, eluting bound ligand and isolating same.

Soluble NR2 polypeptides are also contemplated to be useful in the treatment of disease, injury or abnormality in the nervous system, e.g. in relation to central or peripheral nervous system to treat Cerebral Palsy, trauma induced paralysis, vascular ischaemia associated with stroke, neuronal tumours, motoneurone disease, Parkinson's disease, Huntington's disease, Alzheimer's disease, Multiple Sclerosis, peripheral neuropathies associated with diabetes, heavy metal or alcohol toxicity, renal failure and infectious diseases such as herpes, rubella, measles, chicken pox, HIV or HTLV-1. The NR2 polypeptides may also be important for regulating cytokine activity such as leptin activity, modulating haempoiesis and/or regulating or modulating adipose tissue.

As stated above, the NR2 or its ligand of the present invention or their functional derivatives may be provided in a pharmacuetical composition together with one or more pharmaceutically acceptable carriers and/or diluents. In addition, the present invention contemplates a method of treatment comprising the administration of an effective amount of NR2 of the present invention. The present invention also extends to antagonists and agonists of NR2 and/or its ligand and their use in therapeutic compositions and methodologies.

A further aspect of the present invention contemplates the use of NR2 or its functional derivatives in the manufacture of a medicament for the treatment of NR2 mediated conditions defective or deficient.

The present invention is further described with reference to the following non-limiting Examples.

The following single and three letter abbreviations for amino acid residues are used in the specification:

| Amino Acid | Three-letter Abbreviation | One-letter Symbol |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

TABLE 2

SEQUENCE OF OLIGONUCLEOTIDES

| OLIGONUCLEOTIDE | SEQUENCE | SEQ ID NOs |
|---|---|---|
| HYB2 | 5'(A/G)CTCCA(A/G)TC(A/G)CTCCA-3' | 1 |
| T3 | 5'-TAATACGACTCACTATAGGGAGA-3' | 2 |
| T7 | 5'-ATTAACCCTCACTAAAGGGA-3' | 3 |
| 721 | 5'-ACTAGCAGGGATGTAGCTGAG-3' | 4 |
| 722 | 5'-CTCAGCTACATCCCTGCTAGT-3' | 5 |
| 761 | 5'-CTGCTCCTATGATACCT-3' | 6 |
| 875 | 5'-CCTCTTCCATCTTATTGCTTGG-3' | 7 |
| 939 | 5'-ATCGGTCGTGACATACAAGG-3' | 8 |
| 1056 | 5'AGCTAAGCTTTCTAGATATCCAATTACTCCTTGGAGA-3' | 9 |
| 1092 | 5'-AGCTTCTAGATCAATCACTCTGGTGTTTTTCAAT-3' | 10 |
| 1094 | 5'-AGCTTCTAGATCAAACTTTTATATCCATGACAAC-3' | 11 |

EXAMPLE 1

CLONING OF A HUMAN NR2 (HAEMOPOIETIN RECEPTOR) cDNA

A cDNA library constructed from mRNA from a the bone marrow of a patient recovering from chemotherapy was constructed by C.G. Begley, Cancer Research Unit, WEHI in 1ZAP (Stratagene, CA, USA) were used to infect *Escherichia coli* of the strain LE392. Infected bacteria were grown on twenty 150 mm agar plates, to give approximately 50,000 plaques per plate. Plaques were then transferred to duplicate 150 mm diameter nylon membranes (Colony/Plaque Screen™, NEN Research Products, MA, USA), bacteria were lysed and the DNA was denatured fixed by autoclaving at 100° C. for 1 min with dry exhaust. The filters were rinsed twice in 0.1%(w/v) sodium dodecyl sulfate (SDS), 0.1×SSC (SSC is 150 mM sodium chloride, 15 mM sodium citrate dihydrate) at room temperature and pre-hybridised overnight at 42° C. in 6×SSC containing 2 mg/ml bovine serum albumin, 2 mg/ml Ficoll, 2 mg/ml polyvinylpyrrolidone, 100 mM ATP, 10 mg/ml tRNA, 2 mM sodium pyrophosphate, 2 mg/ml salmon sperm DNA, 0.1% SDS and 200 mg/ml sodium azide. The prehybridisation buffer was removed. 1.2 mg of the degenerate oligonucleotides for hybridisation (HYB2; Table 2 above) were phosphorylated with T4 polynucleotide kinase using 960 mCi of $g^{32}$P-ATP (Bresatec, S.A., Australia). Unincorporated STP was separated from the labelled oligonucleotide using a pre-packed gel filtration column (NAP-5; Pharmacia, Uppsala, Sweden). Filters were hybridised overnight at 37° C. in 80 ml of the prehybridisation buffer containing and $10^6$–$10^7$ cpm/ml of labelled oligonucleotide. Filters were briefly rinsed twice at room temperature in 6×SSC, 0.1%(v/v) SDS, twice for 30 min at 45° C. in a shaking waterbath containing 1.51 of the same buffer and then briefly in 6×SSC at room temperature. Filters were then blotted dry and exposed to autoradiographic film −70° C. using intensifying screens, for 7–14 days prior to development.

Plaques that appeared to hybridise to the probe on duplicate filters were picked and eluted for 2 days at 4° C in 0.5 ml of 100 mM NaCl, 10 mM $MgCl_2$, 10 mM Tris.HCl pH7.4 containing 0.5%(w/v) gelatin and 0.5% (v/v) chloroform. 5 ml aliquots of each eluate was used as the substrate for two PCR reactions containing 5 ml of 10× concentrated PCR buffer (Boehringer Mannheim GmbH, Mannheim, Germany), 1 ml of 10 mM dATP, dCTP, dGTP and dTTP, 2.5 ml of the oligonucleotides HYB2 and either T3 or T7 at a concentration of 100 mg/ml, 0.5 ml of Taq polymerase (Boehringer Mannheim GmbH) and water to a final volume of 50 ml. PCR was carried out in a Perkin-Elmer 9600 by heating the reactions to 96° C. for 2 min and then for 25 cycles at 96° C. for 30 sec, 55° C. for 30 sec and 72° C. for 2 min. The reactions were then electrophoresed on a 1 %(w/v) low melting point agarose gel in TAE. Any positive products were excised, the gel slice was melted and 2 ml was used as the substrate for a second PCR reaction using conditions identical to the first. The product from the second reaction was purified using an ultrafree-MC centrifugal filtration unit (Millipre Corp.) by centrifugation for 15 min at 2000 g in an eppendorf centrifuge, adding 0.5 ml of 10 mM Tris.HCl, 1 mM EDTA pH8 and recentrifuging. This procedure was repeated three times and the DNA was recovered in 50 ml of 10 mM Tris.HCl, 1 mM EDTA pH8.

Approximaely 500 ng of DNA from each PCR reaction was sequenced using a fmol sequencing kit (Promega Corporation, WI, USA), according to the manufacturer's instructions with the $^{33}$P-labelled oligonucleotide primer HYB2. The products were resolved on a 6% w/v polyacrylamide gel and the sequence of each clone was analysed using the Blast database comparison programs and the translation function of the Wisconsin suite of DNA programs. The sequence of the PCR product derived from the primary plaque eluate number CF.32 appeared to be novel since it had no homologues in the databases of DNA sequences that were searched, and upon inspection of the sequence of the conceptually translated products appeared also to be a member of the haemopoietin rector family. This clone was given the name of new receptor 2 or NR2.

The positively hybridising bacteriophage present in the eluate from the primary NR2-CF-32-1 was purified using a second round of screening performed in a manner identical to the first, except that plaques were grown on smaller, 82 mm, plates of agar. Once purified DNA, the positive cDNA cloned into the plasmid pBluescript was excised from the λ-ZAP II bacteriophage according to the manufacturer's instructions (Statagene). A CsCl purified preparation of the DNA was made and this was sequenced on both strands. Sequencing was performed using an Applied Biosystems automated DNA sequencer, with fluorescent dideoxynucleotide analogues according to the manufacturer's instructions. The DNA sequence was analysed using software supplied by Applied Biosystems.

EXAMPLE 2

ISOLATION OF ADDITIONAL NR2 cDNAS

NR2-CF.32 did not appear to contain the entire coding region of the novel receptor. In order to identify other cDNA libraries containing cDNA clones for NR2 we performed PCR upon 1 ml aliquots of λ-bacteriophage cDNA libraries made from mRNA from various human tissues and using oligonucleotides 722 and 761, designed from NR2-CF-32-1, as primers. The oligonucleotides are defined in Table 2, above. Reactions contained the same elements as described above and were performed in an identical manner. In addition to the orginal library, five other cDNA libraries appeared to contain NR2 cDNAs. These were screened using a $^{32}$P-labelled oligonucleotide 721 and 761 designed from the 5'-end and the 3' end of the sequence derived from NR2-CF.32, using conditions identical to those described in section (i) except that filters were washed at 55° C. rather than 45° C. Again, as described in section (i), positively hybridising plaques were purified, the cDNAs were recovered and cloned into plasmids pBluescript II or pUCl19. Ten independent cDNA clones were sequenced on both stands. Further clones were isolated in a similar manner by screening libraries with oligonucleotide 875 and 939.

The extent of each clone is illustrated in FIG. 1 and a composite sequnce is shown in FIGS. 2A to 2K. NR2 clearly has all the features of a member of the haemopoietin receptor family.

EXAMPLE 3

ANALYSIS OF TIRE EXPRESSION PATTERN OF NR2 mRNA

Figure 9:
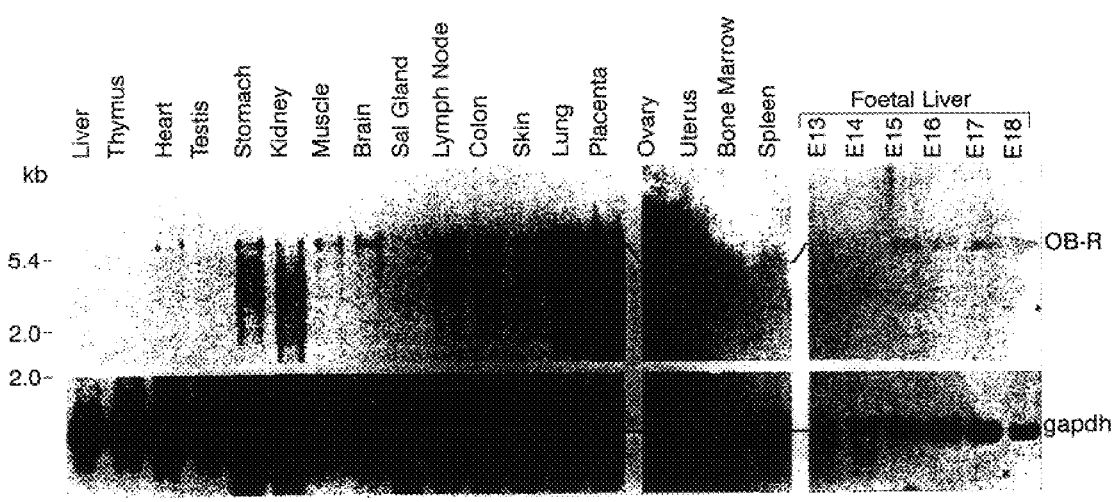
FIG. 9 is a photographic representation showing expession of leptin receptor (NR2) in murine tissues.

Northern blots of mRNA from various human tissues and cell lines were hybridised with a random-primed human NR2 cDNA fragment from the internal EcoR I site to the Hpa I site (FIG. 1). Using the protocol described previously by Hilton et al. (15), two human NR2 mRNA species were observed to be expressed at a low level in a range of adult tissues, and at higher levels in foetal tissues such as the lung and liver. FIG. 9 shows expression ofNR2 in various mouse tissues using human NR2 cDNA as probe. Interestingly among a series of human haemopoietin cell lines the megakaryotic cell line MEGO1 expressed high levels of NR2 mRNA suggesting that NR2 and its cognate ligand may play a role in the regulation of the megakaryocyte proliferation, differentiation and/or function.

EXAMPLE 4

GENERATION OF PLASMIDS DIRECTING THE EXPRESSION OF FULL-LENGTH AND SECRETED FORMS HUMAN NR2

Since antibodies to NR2 were not available to monitor expression, constructs were engineered to express full length and two soluble versions of NR2 with an N-terminal "FLAG" epitope (International Biotechnologies/Eastman Kodak, New Haven CT). First, a derivative of the mammalian expression vector pEF-BOS was generated so that it contained DNA encoding the signal sequence of murine IL-3 (MVLASSTTSIHTMLLLLLMLFHLGLQASIS [SEQ ID NO. 14]) and the FLAG epitope (DYKDDDDK [SEQ ID NO 15]) followed by a unique Xba I cloning site. This vector was named pEF/IL3SIG/FLAG.

The 5' end of the mature NR2 coding region was generated by PCR using primers 1056 and 721 on clone 60-58-7 (FIG. 1). The EcoR I/Hpa I fragment of clone 60-55-7-6 containing the 3' end of the NR2 coding region and a portion of the 3-untranslated region was cloned into the EcoR I/SmaI digested pBluescript (FIG. 1). This construct was digested with Hind III and EcoR I and into it was cloned the 5'-NR2 PCR product digested with the same enzymes. The resulting construct was digested with Xba I to yield a fragment which contained the coding region of human NR2 from Y26 to the natural last amino acid L897 (FIG. 1) and a segment of 3'-untranslated region and was cloned into the Xba I site of pEF/IL3SIG/FLAG to give pEF/IL3SIG/FLAG/NR2/897. A soluble derative ofhuman NR2 was also engineered. PCR was carried out either using primers 1056 and 1092 to amplify the predicted mature coding region of the extracellular portion of human NR2 (Y26 to D839; FIG. 1). The PCR products were digested with Xba I and subcloned into Xba I digested pEF/EL3SIG/FLAG to give pEF/IL3SIG/FLAG/NR2/839. The identity of each construct was confirmed by dideoxy sequencing.

EXAMPLE 5

TRANSIENT EXPRESSION OF FULL LENGTH AND SECRETED FORMS OF HUMAN NR2 IN COS CELLS

In order to confirm that full length and soluble NR2 could be produced using the expression vectors pEF/IL3SIG/FLAG/NR2/897 and pEF/IL3SIG/FLAG/NR2/839, COS cells were transiently transfected with these constructs. Briefly, COS cells from a confluent 175 cm2 tissue culture flask were resuspended in PBS and electroporated (BioRad Gene pulser; 500 mF, 300 V) with 20 mg of uncut pEF/IL3SIG/FLAG/NR2/897 or pEF/IL3SIG/FLAG/NR2/839 in a 0.4 cm cuvette (BioRad). After 2 to 3 days at 37° C. in a fully humidified incubator containing 10% v/v $CO_2$ in air cells were used for analyses of protein expression. Conditioned medium was collected by centrifugation and stored sterile at 4° C. Cells were also harvested and lysed for 5 min in 500 ml of 50 mM Tris.HCl pH7.4 containing 150 mM NaCl, 2 mM EDTA and 1% w/v sodium deoxycholate and 0.2% w/v SDS. 15 ml of anti-FLAG M2 affinity gel (International Biotechnologies/Eastman Kodak, New Haven CT) was then added to the cell extract or to 1 ml of conditioned medium and precipitation was carried out overnight at 4° C. The affinity gel was then washed three times in cold PBS and the precipitated protein was eluted by resuspending the gel in 80 ml of 100 mM sodium phosphate pH7.2, 10 mM EDTA, 0.1% w/v SDS and 1% 2- mercaptoethanol and boiling for 5 min. The supernatant was removed and 8 ml of 10% b-octyl glucoside was added. One half of each sample was incubated for 16 hours with 0.6 U of N-Glycanase-F (Boehringer-Mannheim), while the remainder was left untreated. An equal volume of 2x SDS-PAGE sample buffer was added to the samples which were then boiled and electrophoresed on pre-cast 4–15% w/v polyacrylamide gels (BioRad). The resolved proteins were then electroblotted onto Immobolon membranes, which were then blocked with 5% w/v skim milk, 0.1% v/v Tween 20 in PBS, rinsed and incubated with 5 ml of anti-FLAG M2 antibody in 2.5 ml of PBS containing 0.1% v/v Tween 20, rised and incubated with peroxidase-conjugated human anti-mouse Ig in 5% w/v skim milk, 0.1% v/v Tween 20 in PBS, rinsed and incubated with ECL reagent for 1 min. Filters were then blotted dry and exposed to autoradiogrgphic film for 1 mn.

COS cells that were mock tansfected contained no reactive protein, while COS cells transfected with pEF/IL3SIG/FLAG/NR2/897 expressed an immunoreactive protein of between 120,000 and 140,000 molecular weight. Deglycosylation with N-Glycanase-F resulted in a reduction in the apparent molecular weight to approximately 110,000 close to that predicted from the cDNA sequence ofNR2. The immunoreactivity observed was completely inhibited by inclusion of an excess of the FLAG peptide during the immunoprecipitation step. No specific immunoreactive proteins could be detected in the medium conditioned by COS cells transfected with pEF/IL3SIG/FLAG/NR2/897. In contrast immunoreactive proteins were found in the medium and the cell pellet of COS cells transfected with DNA encoding the secreted form of NR2-pEF/IL3SIG/FLAG/NR2/839. The secreted form of NR2, as predicted, exhibited a lower apparent molecular weight than full length NR2, 110,000 to 120,000. This again decreased upon deglycosylation, to approximately 100,000.

COS cells transfected with pEF/IL3SIG/FLAG/NR2/897 were also examined for cell surface expression of NR2 by immunofluoresence staining. $5 \times 10^5$ COS cells were resuspended in 100 ml of PBS containing 5% fetal calf serum and incubated with FITC-conjugated anti-FLAG M2 antibody for 45 min on ice, the cells were fixed and examined using a fluoresence microscope. No positive cells were observed in mock transfected samples, while approximately 10% of COS cells transfected with pEF/IL3SIG/FLAG/NR2/897 stained brightly positive. This data was consistent with the expected transient transfection efficiency of COS cells using electroporation.

EXAMPLE 6

STABLE EXPRESSION OF FULL LENGTH HUMAN NR2

As described below certain routes to the identification of the NR2 ligand require stable expression of full-length NR2 in haemopoietin cell lines and the production and purification of large (mg) amounts of secreted NR2. Stable transfection of the pEF/IL3SIG/FLAG/NR2/897 and pEF/IL3SIG/FLAG/NR2/839 plasmids was achieved by electroporation. Briefly, the plasmids were linearised by digestion with the restriction enzyme Aat II. 20 mg of the linearised pEF/IL3SIG/FIAG/NR2/897 plasmid and 2 mg of pPGKpuropA, pPGKneopA or pPGKhygropA (plasmids directing the expression of the puromycin, neomycin and hygromycin resistance genes) were electropoated into $4 \times 10^6$ parental Ba/F3 cells, Ba/F3 cells engineered to express human gp1130 with or without coexpression of the human LIF receptor, Ba/F3 cells expressing the human b-chain common to the IL-3, IL-5 and GM-CSF receptors, Ba/F3 cells expressing the human IL-2 receptor b- and g-chains, CTLL cells or CHO cells. Briefly, cells were washed twice in ice-cold PBS and resuspended in PBS at $5 \times 10^6$ per ml. $4 \times 10^6$ cells were aliquoted into 0.4 mm electoporation cuvettes with the DNA. DNA and cells were incubated for 10 min on ice and electroporated at 270 V and 960 mF in a Bio-Rad Gene-Pulser (Bio-Rad Laboratories, CA, USA). The cells were mixed with 1 ml of culture medium, centrifuged through 3 ml of FCS and resuspended in 100 ml of culture medium. Cells were then aliquoted into four 24 well . After two days, selection was commenced by the addition puromycin to a concention of 20 mg/ml, G418 to a concentration of 11.2 mg/ml or hygromycin to a concentration of 1 mg/ml. After 10–14 days, clones of proliferting cells were transferred to flasks and after expansion were tested for receptor expression.

Figure 4:
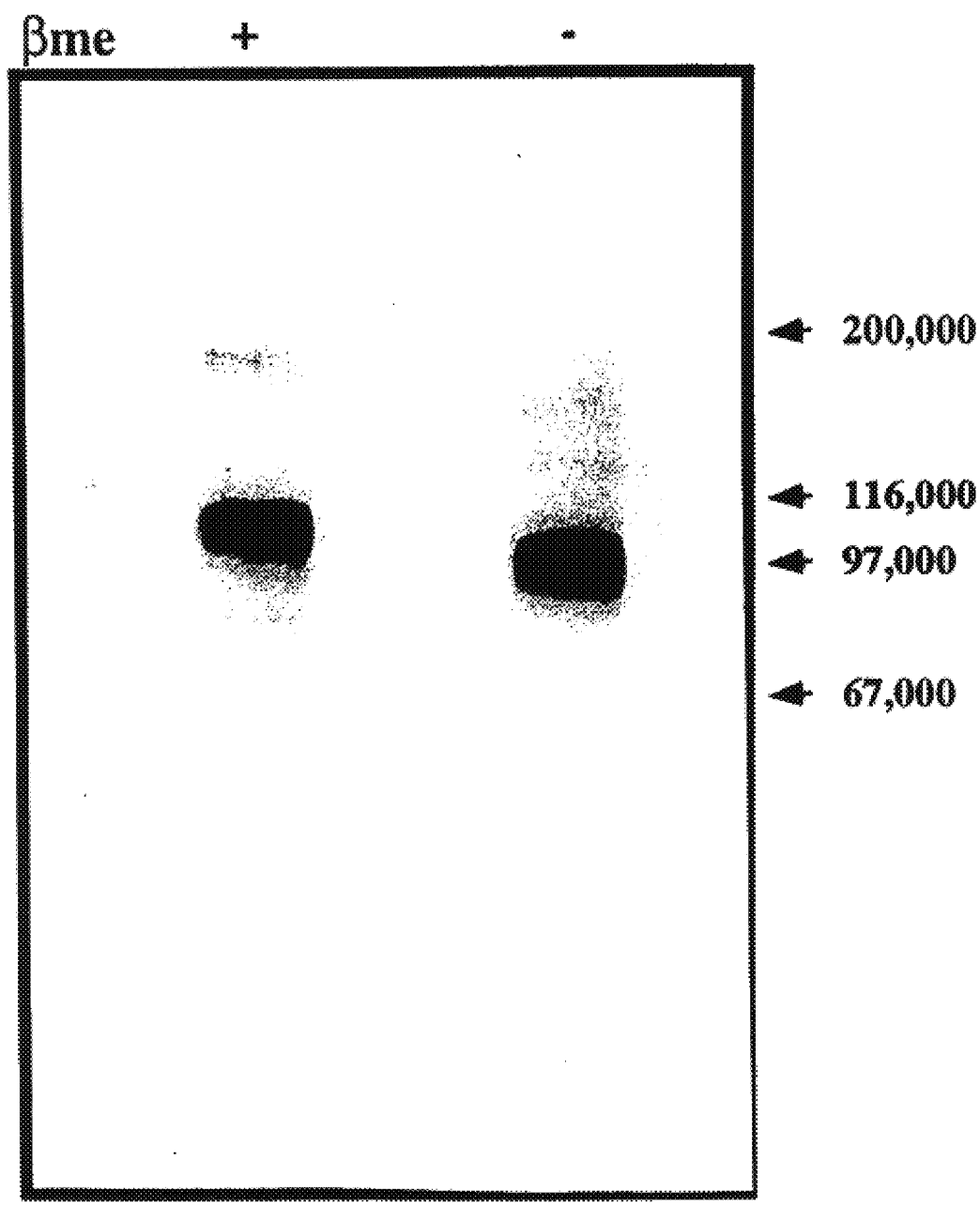
FIG. 4 is a photographic representation of a silver-stained gel of NR2 expression by BA/F$_3$ cells.

FACS analysis using the anti-FLAG M2 antibody (FIG. 3) illustrates that Ba/F3 cells transfected with the pEF/IL3SIG/FLAG/NR2/897 express NR2 on the cell surface. Similar results have been obtained with other cell lines. As with COS cells, CHO cells transfected with pEF/IL3SIG/FLAG/NR839 secrete the NR2 extracellular domain. The extracellular domain of NR2 has been purified on an anti-FLAG M2 antibody affinity column using the FLAG peptide as the means of elution. This results in a high degree of purification of the NR2 extacellular domain as seen in the silver-stained poly-acrylamide gel illustrated in FIG. 4.

EXAMPLE 7

STRATEGIES FOR ISOLATION OF THE LIGAND FOR NR2

The stable expression of full-length and secreted NR2 enables steps to be taken to generate specific monoclonal antibodies to NR2 and allows a number of strategies to be employed to identify the cognate ligands of NR2.

(a) Expression of NR2 in factor dependent cell lines;

A variety of haemopoietin cell lines have been described which are dependent on the presence of exogenous growth factor for survival and proliferation in vitro. Among these are the murine cell lines Ba/F3, FDCP-1, 32D, CTLL, NFS-60, B6SutA, DA-1 and DA-3 and the human cell lines M07 and TF-1. FLAG-tagged murne and human NR2 may be stably expressed in each of these cell lines. The capacity of medium conditioned by a variety of murine and human cell lines and tissues to stimulate the survival and division of factor dependent cell lines expressing NR2 will be compared to the ability of the same medium to stimulate parental cell lines that do not express NR2. Medium that shows a greater ability to stimulate the proliferation cells expressing NR2 will be considered as a potential source of NR2.

NR2 has also been co-expressed in Ba/F3 cells with the LIF receptor a-chain and gp1130, with the IL-2 receptor b- and g-chains of the IL-2 receptor and with the common b-chain ofthe IL-3, IL-5 and GM-CSF receptors. Again conditioned medium will be tested for their ability to stimulate the proliferation of these cell lines.

(b) Identification of the NR2 ligand using the Cytosensor;

The haemopoietin cell lines expressing NR2 described above and additional non-haemopoietin cell lines engineered to express NR2 will be used in conjunction with the Cytosensor screen conditioned medium for the presence of a ligand capable of altering cellular ion fluxes. Positive conditioned medium will be considered as a potential source of NR2 ligands.

(c) Selection of Ba/F3 cells expressing the NR2 ligand;

Ba/F3 cells expressing NR2 with or without additional receptor components will be mutated with EMS or with a retrovirus. Mutants that are capable of proliferation in the absence of added growth factor will be selected. The medium from such clones will then be tested for their ability to stimulate the proliferation of Ba/F3 cells expresing NR2 with or without additional receptor components compared with the corresponding Ba/F3 cells that do not express NR2. Positive conditioned medium will be considered as a potential source of the NR2 ligand.

(d) Exprssion of NR2 in cell lines that may be induced to differentiate;

Similar experiments may be performed by expressing FLAF-tagged NR2 in cells that may be induced to differentiate by cytokines. Such cells include the murine lines M1 and WEHI- 3BD+ and the human lines HL-60 and U937. The capacity of medium conditioned by a variety of murine and human cell lines and tissues to induce the differentiation of such cell lines expressing NR2 will be compared to the ability of the same medium to stimulate parental cell lines that do not express NR2. Medium that shows a greater ability to stimulate the differentiation of cells expressing NR2 will be considered as a potential source ofNR2 ligand.

(e) Use of secreted NR2 extracelluar domain as a probe on the Biosensor,

Purified excellular domain of NR2 has been obtained and is being immobilized on the surface of a Biosensor chip. Medium conditioned by a variety of murine and human cell lines and tissues will be passed across the chip and specific changes in the surface plasmon resonance will be noted. Positive medium will be considered as a potential source of NR2 ligand.

(f) Use of secreted NR2 extracellular domain as the basis of an affinity column;

Purified extracellular domain of NR2 has been obtained and is being immobilized using a variety of chemistries. Affinity columns will be constructed and medium conditioned by a variety of murine and human cell lines and tissues will be passed through. Proteins that bind to the column will be considered to be candidate NR2 ligands and will be further characterised.

EXAMPLE 8

HUMAN LEPTIN

A human leptin cDNA (16)was cloned into the peFBOS expression vector (17) in frame with the interleukin-3 leader sequence followed by the FLAG™ epitope sequence (18). CHO cells were tansfected with this vector by electroporation and supernatant harvested from exponentially growing cultures. The supernatant was concentrated over a YM-10 membrane (10-fold) and then applied to an affinity column containing immobilised anti-FLAG™ antibody M2. The column was eluted with FLAG™ peptide according to the manufacturer instructions (Eastman Koda, Rochester, NY). The monomeric form of human leptin was purifed by gel filtration chromatography on a Superose 12 column (Pharmacia, Uppsala, Sweden) and exchanged into 20 mM phosphate buffered (pH7.4) saline (0.15 M) containing 0.02% v/v Tween 20 and 0.02% w/v sodium azide (PBS) by gel filtration on Sephadex G-25 M (PD-10) columns (Pharmacia). Human leptin was iodinated with $^{125}I$ using a modified iodine monochloride method (19) to a specific radioactivity of approximately $10^7$ cpm/pmole and exchanged into PBS as above.

EXAMPLE 9

BINDING OF $^{125}I$ HUMAN LEPTIN TO CELLS EXPRESSING NR2 OR TO SOLUBLE NR2

Cos-hNR2 are COS-7 cells electroporated with peFBOX-hNR12 and harvested at 3 days ($5\times10^4$ cells used per point).

Ba/F3-hNR2 are Ba/F3 cells stably transfected with peFBOS-hNR2 ($9\times10^5$ cells used per point).

Solh NR2 is a soluble form of human NR2 purified by anti-FLAG™ affinity chromatography from the supernatant (48 hr) of COS cells tranfectd with peFBOS-solh NR2 (approx. 0.1 μg/ml final concentration in binding assay).

For cells, the total reaction volume was 100 μl in RPMI-medium containing 10 mM Hepes pH7.4 and 10% v/v foetal calf serum (RHF). The reaction mixture also contained $^{125}I$ h leptin 0–6×$10^5$ cpm as indicated with or without unlabelled h leptin (approx. 1 μg/ml).

The mixture was incubated for 1–1.5 hr at 23° C. and then layered over 200 μl cold foetal calf serum in small, tapered centrifuge tubes (Elkay, Melbourne) and centrifuged at 12000 g for 10 sec. The cell pellet was removed by cutting tubes with a scalpel blade and the cell bound (pellet) radioactivity and the unbound radioactivity (the rest of the tube) were separately counted in a Packard Y-counter. Specifically bound $^{125}I$ h leptin was determined as the difference in counts between otherwise identical tubes that contained or did not contain the unlabelled excess h leptin. The data were plotted as saturation curves (specifically bound versus added $^{125}I$ h leptin) and as Scatchard transformations (specific bound/free radioactivity versus specific bound radioactivity to determine the equilibrium dissociation constants [$K_d$s] (20).

Figure 5A:
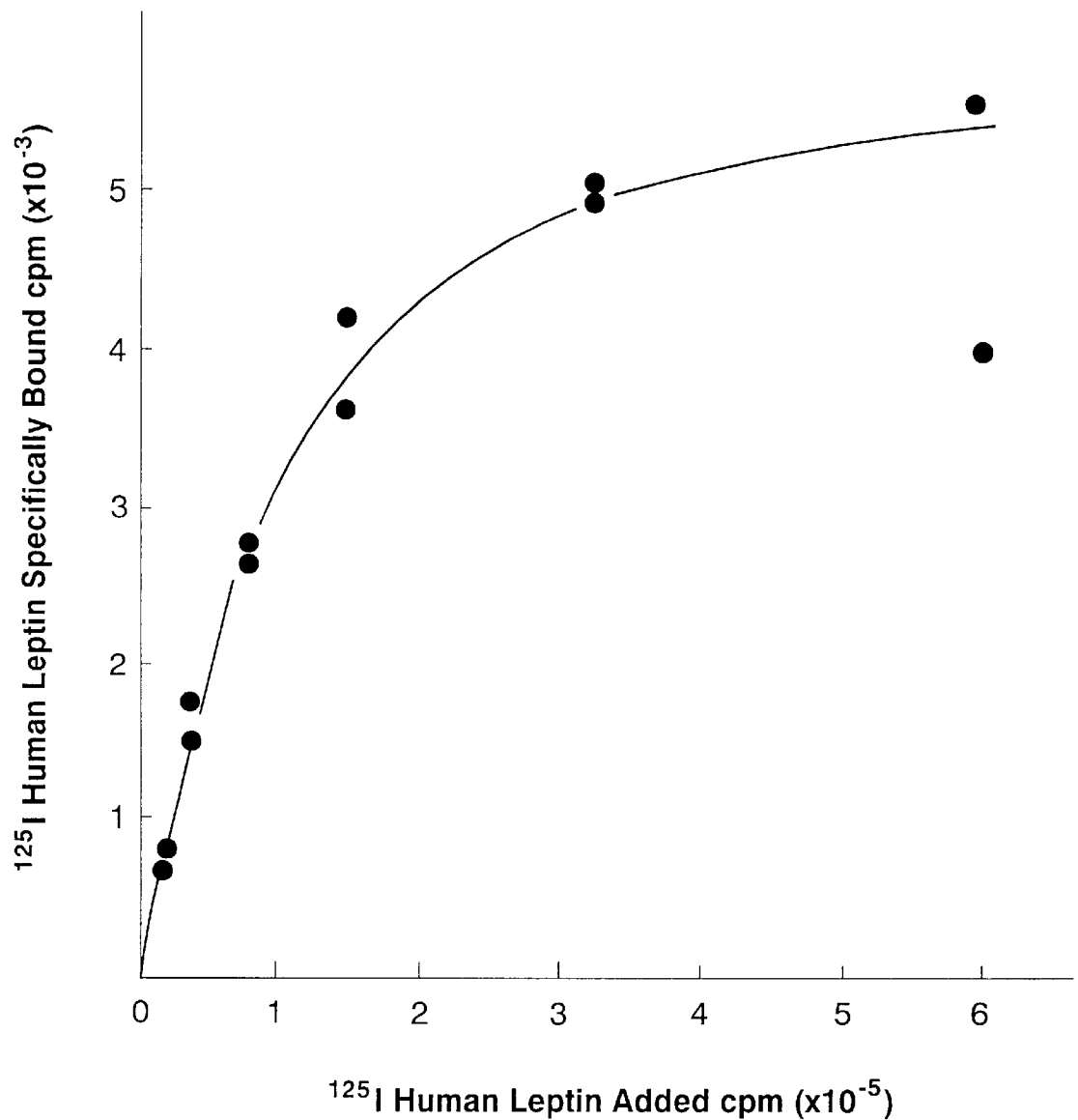
FIGS. 5A and 5B are a graphical representation showing specific binding of $^{125}$I human leptin to Ba/F$_3$ cells stably transfected to express hNR2 on their cell surface.
  (a) Saturation binding curve for $^{125}$I h leptin binding to Ba/F3/hNR2 cells at 23° C.
  (b) Scatchard transformation of the data in (a). The slope of the curve indicates an equilibrium dissociation constant ($K_D$) of 120 pM.
Figure 5B:
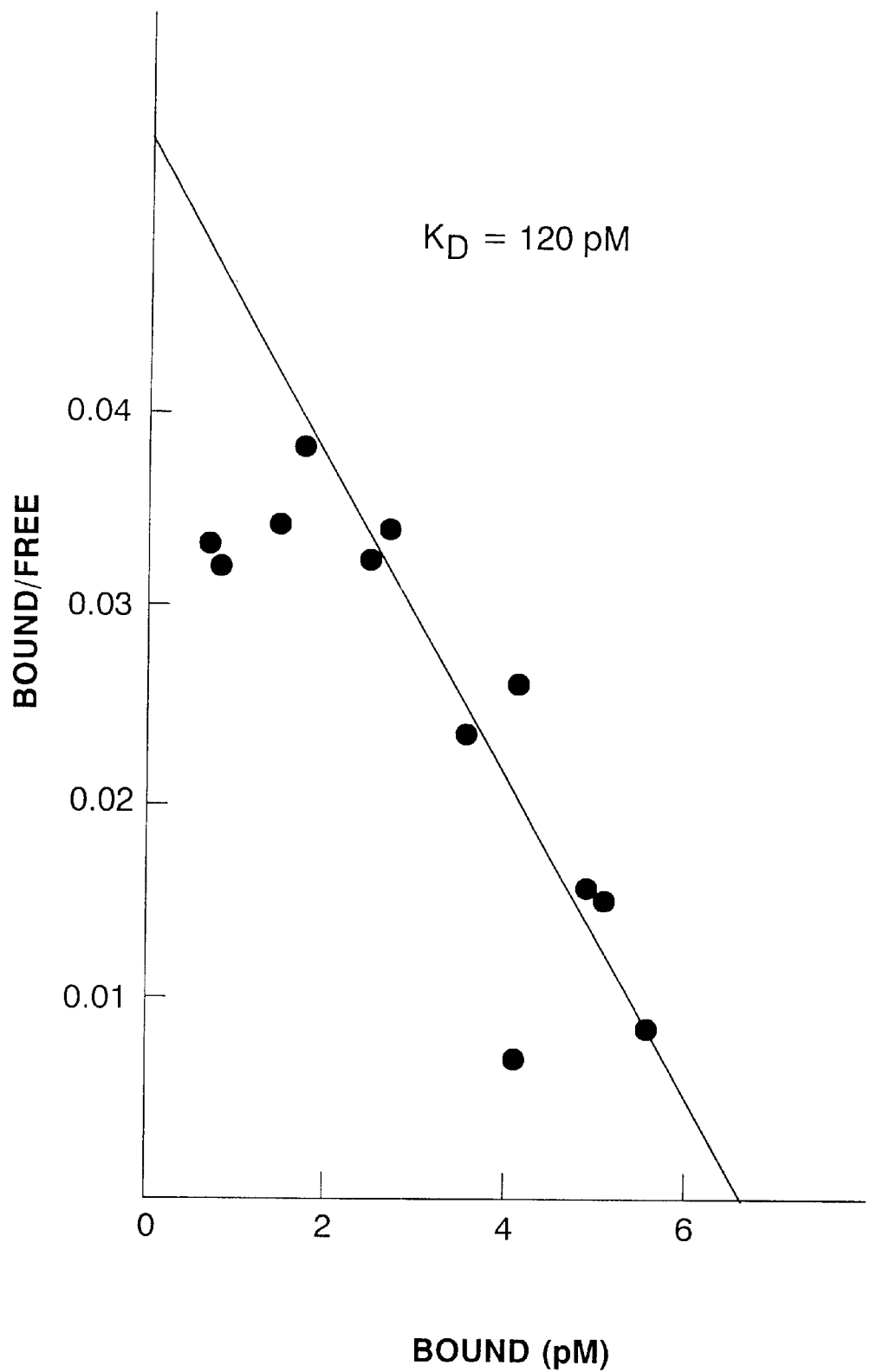
Figure 6:
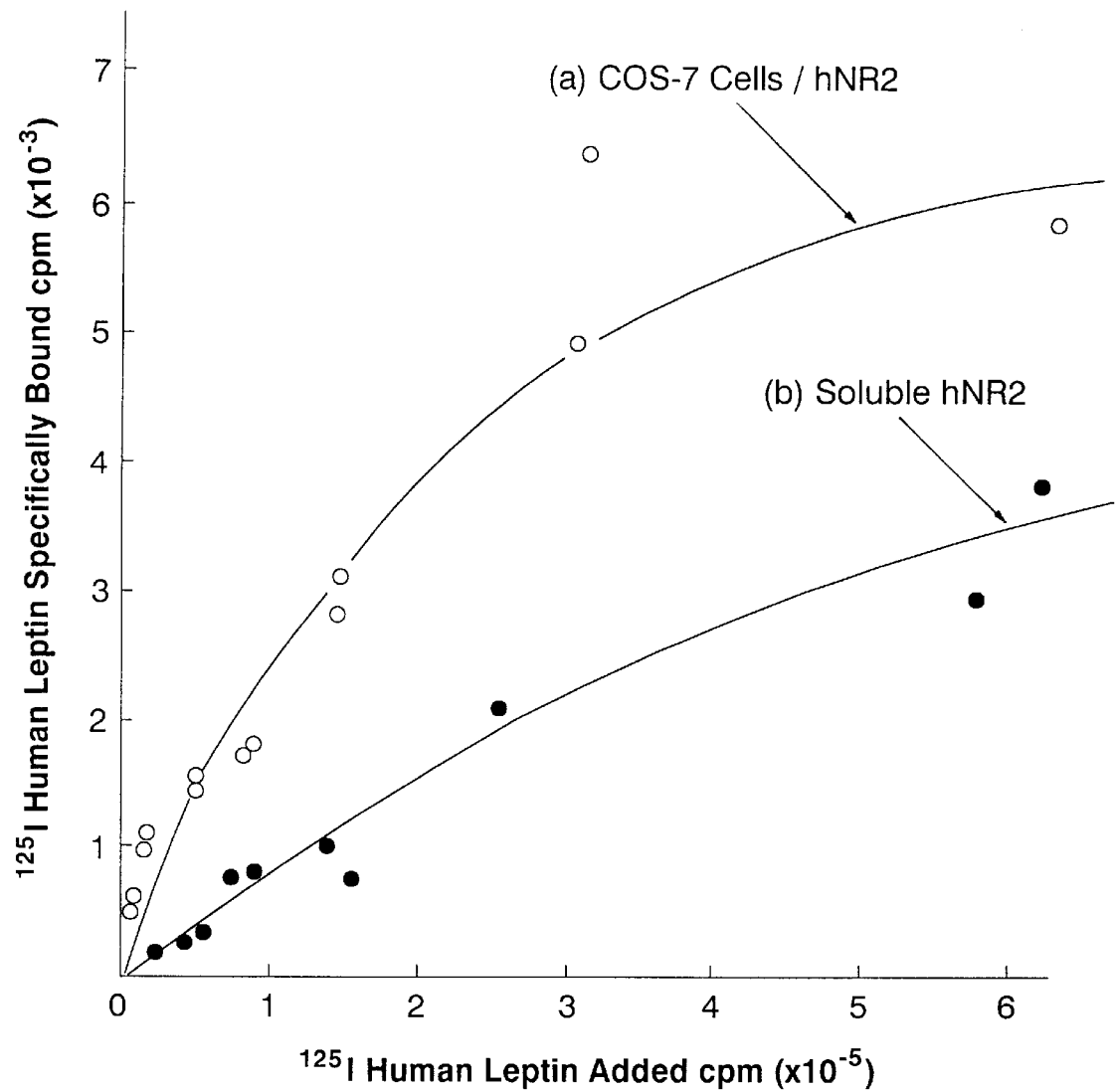
FIG. 6 is a graphical representation showing specific binding of $^{125}$I human leptin to COS-7 cells transiently transfected to express hNR2 on their cell surface (a) or to purified soluble human NR2 (b). Saturation binding curves at 23° C. are shown.

For soluble receptors (sol hNR2) incubations were as above but after 1 hr at 23° C., 20 μl of convavalin A-sepharose 4B beads (1/4 suspension in 0.1 M acetate pH5) were added and incubation continued for a further 30 min. Subsequenly the beads were centrifuged and processed as above. The results are shown in FIGS. 5A, 5B and 6. Human leptin binds to Ba/F3/COS cells transfectd with hNR2 cDNA and to soluble hNR2.

EXAMPLE 9

EXPRESSION OF NR2 IN ANIMAL SPECIES

Figure 7:
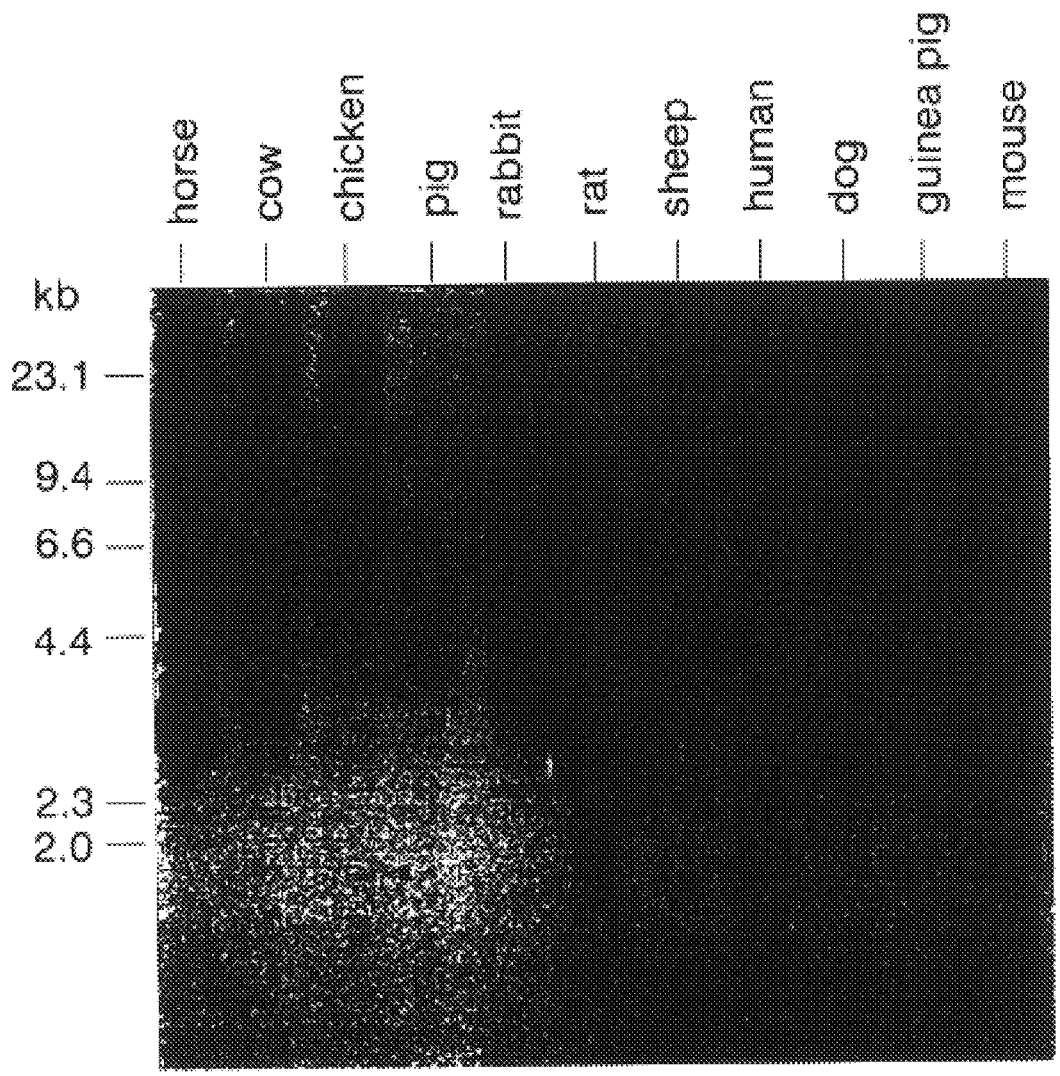
FIG. 7 is a photographic representation showing cross species conservation of the NR2 gene. Southern blot of genomic DNA probed with a specific cDNA probe for NR2.

Genonic DNA from various sources was digested with EcoRI. This was then blotted onto a nylon membrane (GeneScreen Plus$^{SM}$, NEN Rsearch Products, USA). The filter was then probed using a 1.1 kb cDNA fragment of NR2. The fragment covers the 3' half of the first haemopoietn domain and extends to cover the whole of the second haemopoietin domain, terminating the type M fibronectin domain. The filter was prehybidised and hybridised in 0.5M sodium phosphate, 7% w/v SDS and 1mM EDTA at 50° C. ovenight. The filter was then washed in 40 mM sodium phosphate and 1% w/v SDS at 50° C. The results are shown in FIG. 7.

EXAMPLE 10

CLONING OF THE HUMAN NR2 LOCUS

In order to obtain genomic clones of the hunaa NR2 locus, various genomic libraries were screened. These libraries were screened with either oligonucleotide or CDNA probes. Oligonucleotide screening conditions: $10\times10^{16}$ clones were fixed to nylon filters. (Colony/Plaque Screen™, NEN Research Products, USA). These filters were then prehybridised in a 6xSSC buffer containing 0.2% Ficoll, 0.2% w/v bovine serum albumin, 0.2% polyvinylpyrollidine, 0.1M ATP, 50 μg/mL transfer RNA, 2 mM tetra-sodium pyrophophate, 50 μg/mL herring sperm DNA and 0.1% w/v sodium azide at 37° C. for at least 2 hours. They were hybridised overnight under the same conditions, with at least $2\times10^6$ cpm/mL of $^{32}P$-labelied oligonucleotide probe. The filters were then washed in 6xSSC/0.1% w/v SDS at 50–55° C. depending on the sequence of the specific oligonucleotide (Melting Temp −10° C.).

cDNA screening conditions: $1\times10^6$ clones were fixed to nylon filers. These filters were then prehybridised in a 2xSSC buffer containing 0.2% Ficoll, 0.2% w/v bovine serum albumin, 0.2% polyvinylpyrollidine, 0.1M ATP, 50 μg/mL transfer RNA, 2mM tetra-sodium pyrophophate, 50 μg/mL hering sperm DNA and 0.1% w/v sodium azide at 37° C. for at least 2 hours at 65° C. They were hybridised overnight under the same conditions, with at least $2\times10^6$ cpm/mL of $^{32}P$-labelled cDNA fragment. The filters were then were then washed in 2xSSC/0.1% w/v SDS at 65° C.

EXAMPLE 11

RESTRICTION ENZYME MAPPING

The clones obtained were characterised by mapping with partial endonuclease digestion (21).

In order to determine on which figments the various exons were present, specific oligonucleotide probes were used. The various clones were digested with a range of restriction enzymes. These were then blotted to a nylon membrane (GreenScreenPlus℠), NEN Research Products, USA). Oligonucleotides derived from the cDNA sequence (and known to be specific for a particular exon), were then hybridised to the digested fragment. These hybridisations were done Those skilled in the art will appreciate that the invention described herein is susceptible to variations and modifications other than those specifically described. It is to be understood that the invention includes all such variations and modifications. The invention also includes all of the step, features, compositions and compounds refered to or indicated in this specification, individually or collectively, and any and all combinations of any two or more of said steps or features.

TABLE 3

Intron-Exon juctions of the human NR2 gene

| Exon | Exon size (bp) | DONOR | | | Intron size | ACCEPTOR | | |
|---|---|---|---|---|---|---|---|---|
| 55 | 60 | ATTGGG | gtaagttatt | [SEQ ID NO. 16] | | ccttttccag | GTGTAT | [SEQ ID NO. 29] |
| Ig | 330 | AAATAG | gtaagcatta | [SEQ ID NO. 17] | | tcctaacag | AATTTA | [SEQ ID NO. 30] |
| SD100A | 124 | TGTTCT | gtaagtacca | [SEQ ID NO. 18] | | ttaaattcag | ATGCAA | [SEQ ID NO. 31] |
| SD100A SD100B | | | | | | | | |
| SD100B | 145 | CACAAG | gtaggttatg | [SEQ ID NO. 19] | | tatttaacag | GCTGAC | [SEQ ID NO 32] |
| Ig | 291 | TGATTG | gtaagaaaca | [SEQ ID NO. 20] | 0.16 | ctcattacag | ATGTCA | [SEQ ID NO. 33] |
| SD100A' | 118 | ATTGAG | gtatcatagg | [SEQ ID NO. 21] | 2.3 | tttcaaatag | ATGTGA | [SEQ ID NO. 34] |
| SD100A' | 200 | CTGTGG | gtatgtcaag | [SEQ ID NO. 22] | 2.4 | tcttttaaag | GAGCAG | [SEQ ID NO. 35] |
| SD100B' | 149 | TGGAAG | gtaccttta | [SEQ ID NO. 23] | | aaatttctag | TGAAGC | [SEQ ID NO. 36] |
| SD100B' | 160 | TAAAAG | gtctgcagag | [SEQ ID NO. 24] | 0.2 | tattttacag | ATGTAT | [SEQ ID NO. 37] |
| FnIII | 83 | TGGAGG | gtataccaat | [SEQ ID NO. 25] | >7 kbp | catttggcag | TTCCTA | [SEQ ID NO. 38] |
| FnIII | 161 | CAATTC | aattggtgct | [SEQ ID NO. 26] | | tttactacag | CCCCTG | [SEQ ID NO. 39] |
| FnIII' FnIII' | | | | | | | | |
| Tm | 106 | CCAAAG | gtattgtact | [SEQ ID NO. 27] | 1.4 | tcttttcag | ATGATA | [SEQ ID NO. 40] |
| Cyt (Box I) | 76 | CATAAG | gttgcttttt | [SEQ ID NO. 28] | 3 | ccctttgtag | AATGAA | [SEQ ID NO. 41] |
| Cyt' (NR2.2) | 212 | | | | 3 | ccttttccag | AAAATG | [SEQ ID NO. 42] |
| 3'utr | >1085 | | | | 3 | atctaaacag | AGAACG | [SEQ ID NO. 43] |
| Consensus | | AG | $gt^a/_bagt$ | | | tc rich-cag G | | | under the same conditions as mentioned above for oligonucleotides. Exons could then be mapped to specific fragments by a positive hybridisation after overnight exposure.

Figure 8:
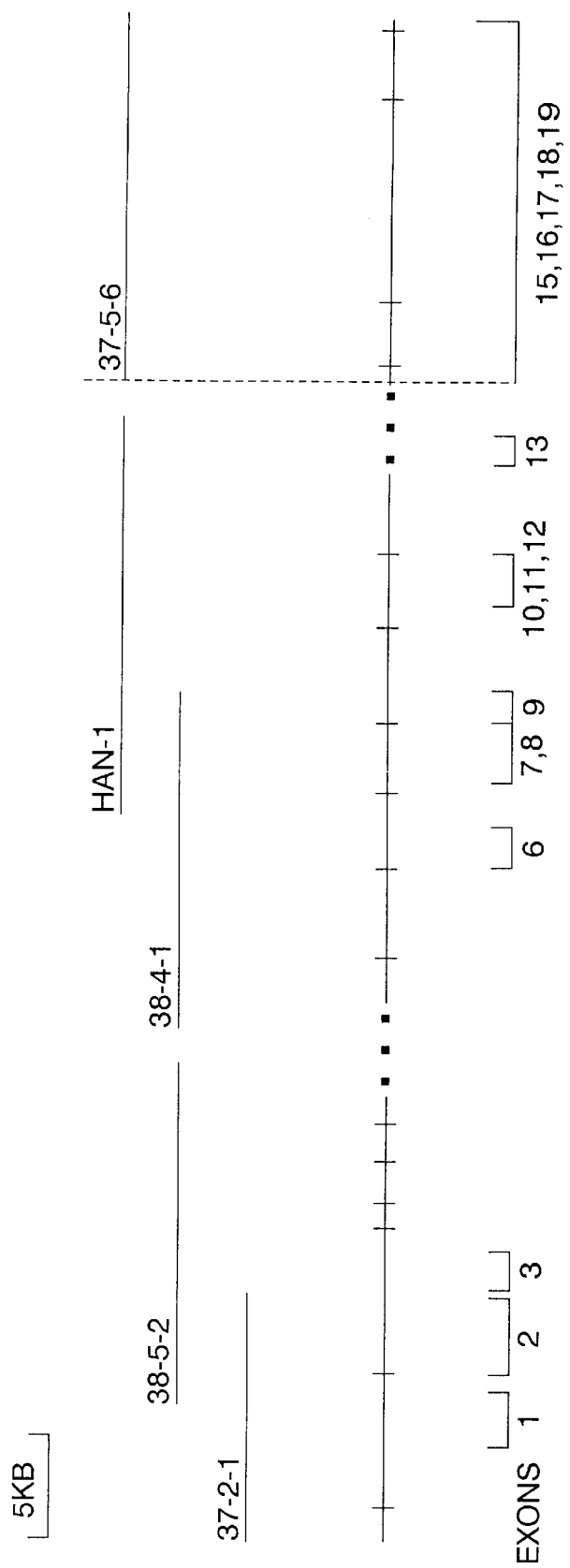
FIG. 8 is a diagrammatic representation of the NR2 locus. A map of the NR2 locus, showing positioning of the clones isolated from genomic libraries. The results of the restriction enzyme mapping using NcoI and the positioning of the exons of these fragments are also shown.

Intron/exon boundary sequences were determined by sequencing across the intron/exon boundaries. Primers specific for sequence on either side of the boundary were used in a sequencing PCR reacion. Sequencing was performed on an ABI 373 sequencer using the Taq cycle sequencing kit (Applied Biosystems). These sequences were then compared to the consensus intron/exon boundary sequence (22). The results are shown in FIG. 8 and in Table 3.

EXAMPLE 12

DETERMINATION OF AMINO ACID SEQUENCE OF hNR2

The N-terminal amino acid sequence of hNR2 was determined The results are shown below. The acual sequence starts at amino acid 16. The sequence is as follows:

[SEQ ID NO:44]
Asp Ser Ile Ser Ser Ser Asp Tyr Lys Asp Asp Asp
              5                   10
Glu Ser Arg Tyr Pro Ile Thr Pro Trp Arg Phe Lys
         15                  20
Leu Ser Xaa Met Pro Pro Xaa Ser Thr Tyr Asp
  25              30              35

REFERENCES:

1. Du, X.X and Williams, D.A. (1994) Blood 83: 2023–2030.
2. Yang, Y.C. and Yin, T. (1992) Biofactors 4: 15–21.
3. Paul, S.R., Bennett, F., Calvetti, J.A., Kelleher, K., Wood, C.R, O'Hara, R.J.J., Leary, A.C., Sibley, B., Clark, S.C., Williams, D.A. and Yang, Y.-C. (1990) Proc. Natl. Acad. Sci. USA 87: 7512.
4. Musashi, M., Clark, S.C., Sudo, T., Urdal, D.L., and Ogawa, M. (1991) Blood 78: 1448–1451.
5. Schibler, K.L, Yang, Y.C. and Christensen, R.D. (1992) Blood 80: 900–3.
6. Tsuji, K., Lyman, S.D., Sudo, T., Clark, S.C., and Ogawa, M. (1992) Blood 79: 285–60.
7. Burstein, S.A., Mei, R.L., Henthorn, J., Friese, P. and turner, K. (1992)J. Cell Physiol. 153:305–12.
8. Hangoc, G., Yin, T., Cooper, S., Schendel, P., Yang, Y.C. and Broxmeyer, H.E. (1993) Blood 81: 965–72.
9. Teramura, M., Kobayashi, S., Hoshino, S., Oshimi, K. and Mizoguchi, H. (1992) Blood 79: 327–31.
10. Yonemura, Y., Kawakita, M., Masuda, T., Fujimoto, K., Kato, K. and Takatsuki, K. (1992) Exp. Hematol. 20: 1011–6.
11. Baumann, H. and Schendel, P. (1991) J. Biol. Chem. 266: 20424–7.
12. Kawashima, I., Ohsumi, J., Mita-Honjo, K., Shimoda-Takano, K., Ishikawa, H., Sakakibara, S., Miyadai, K, and Takiguchi, Y. (1991) Febs. Lett. 283: 199–202.
13. Keller, D.C., Du, X.X. Srour, E.f., Hoffman, R and Williams, D.A. (1993) Blood 82: 1428–35.
14. Sambrook, J., Fritsch, E.F. and Maniatis, T. (1989) Molecular cloning: A Laboratory Manual Cold Spring Harbor Laboratory, Cold Spring Harbor, New York.

What is claimed is:

1. An isolated nucleic acid molecule encoding at haemopoietin receptor, wherein said haemopoietin receptor comprises the amino acid sequence as set forth in SEQ ID NO:13.

2. An isolated nucleic acid molecule comprising the nucleotide sequence set forth in SEQ ID NO:12.

3. An isolated nucleic acid molecule, wherein said nucleic acid molecule encodes a portion of haemopoietin receptor which comprises the amino acid sequence as set forth in SEQ ID NO: 13, and wherein said portion of the haemopoietin receptor binds leptin and comprises the amino acid sequence of Tyr26 to Asp839 of SEQ ID NO: 13.

4. A vector comprising the nucleic acid molecule according to claim 1, 2 or 3.

5. A host cell comprising the vector according to claim 4.

6. A host cell comprising the nucleic acid molecule according to claim 1, 2 or 3.

* * * * *